(12) United States Patent
Levine et al.

(10) Patent No.: US 6,973,350 B1
(45) Date of Patent: Dec. 6, 2005

(54) DIAGNOSIS OF ATRIAL FUSION, ATRIAL PSEUDOFUSION AND/OR NATIVE ATRIAL ACTIVITY

(75) Inventors: Paul A. Levine, Santa Clarita, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 326 days.

(21) Appl. No.: 10/405,210

(22) Filed: Mar. 31, 2003

(51) Int. Cl.[7] ............................................. A61N 1/365
(52) U.S. Cl. ...................................................... 607/27
(58) Field of Search ........................... 607/4, 9, 14–19, 607/27, 28, 122

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,184,615 A | 2/1993 | Nappholz et al. | 128/419 PG |
| 5,203,326 A * | 4/1993 | Collins | 607/4 |
| 5,350,410 A | 9/1994 | Kleks et al. | 607/28 |
| 5,466,254 A | 11/1995 | Helland | 607/123 |
| 5,476,483 A | 12/1995 | Bornzin et al. | 607/17 |
| 5,713,934 A | 2/1998 | Leckrone | 607/28 |
| 6,314,323 B1 | 11/2001 | Ekwall | 607/23 |
| 6,324,427 B1 | 11/2001 | Florio | 607/28 |
| 6,434,428 B1 | 8/2002 | Sloman et al. | 607/28 |
| 2002/0120303 A1 * | 8/2002 | Levine et al. | 607/14 |

OTHER PUBLICATIONS

David Mendelowitz, "Advance in Parasympathetic Control of Heart Rate and Cardiac Function," News Physiol. Sci. (Aug. 1999) vol. 14, pp. 155-161.

* cited by examiner

Primary Examiner—George Manuel

(57) ABSTRACT

Exemplary methods and devices for determining whether atrial fusion, atrial pseudofusion and/or atrial native activity have occurred. Various methods and/or devices are suitable for use with atrial autocapture. Other methods, devices and/or systems are also disclosed.

14 Claims, 17 Drawing Sheets

EXEMPLARY AR RHYTHM

Exemplary Waveforms

Normal Capture (610): Stimulus / Atrial Capture Controls

Fusion (620):
A) Native Controls
B) Still Atrial Capture

Pseudofusion (630):
A) Native Controls
B) No Atrial Capture

EXEMPLARY WAVEFORMS

EXEMPLARY "R-WAVE"
DETECTION WINDOW

ATRIAL ER
SENSING
CHANNEL
924

VENTRICULAR
SENSING
CHANNEL
928

MOVE/EXTEND RDW FOR
INCREASED PARASYMPATHETIC ACTIVITY
DECREASED SYMPATHETIC ACTIVITY AND/OR
POSSIBLY CHANGE IN ATRIAL RATE.

MOVE/EXTEND RDW FOR
DECREASED PARASYMPATHETIC ACTIVITY
INCREASED SYMPATHETIC ACTIVITY AND/OR
POSSIBLY CHANGE IN ATRIAL RATE

DIAGNOSIS OF ATRIAL FUSION, ATRIAL PSEUDOFUSION AND/OR NATIVE ATRIAL ACTIVITY

CROSS-REFERENCE TO RELATED APPLICATIONS

This application is related to copending U.S. patent application Ser. No. 10/405,212, titled "Diagnosis of Fusion or Pseudofusion," filed Mar. 31, 2003.

TECHNICAL FIELD

Exemplary methods and/or devices presented herein generally relate to cardiac pacing and/or stimulation therapy. Various exemplary methods and/or devices concern native atrial activity, atrial capture, atrial noncapture, atrial fusion and/or atrial pseudofusion.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. Accordingly, SA node and/or AV node impairments may jeopardize normal heart function.

Perhaps the most common indication for permanent cardiac pacing is SA node impairment (e.g., sinus node dysfunction or sick sinus syndrome). SA node impairment may include sinus bradycardia, sinus arrest, and/or sinoatrial exit block. Acute myocardial infarction may also impair SA depolarization and/or action potential conduction in the atria.

Various cardiac pacing schemes aim to compensate for SA node impairment. For example, a pacing scheme referred to as DDD is capable of atrial and ventricular sensing and pacing. When DDD pacing senses native atrial activity during an atrial alert period, it typically inhibits output of atrial stimulus, terminates an atrial escape interval and initiates an AV delay. DDD pacing is indicated for treatment of maladies such as, but not limited to, atrial bradyarrhythmias. Another pacing scheme, known as DVI (AV sequential pacing), provides for atrial and ventricular pacing but ventricular sensing only. DVI pacing is indicated for treatment of maladies such as, but not limited to, sick sinus syndrome with some degree of atrioventricular impairment. Yet another pacing scheme, known as DDI (AV sequential, non-P-synchronous pacing with dual-chamber sensing), provides for atrial and ventricular pacing and sensing, typically in an effort to prevent competitive atrial pacing (e.g., sensed atrial activity inhibits atrial pacing). DDI pacing has proven useful for treatment of maladies such as sinus node dysfunction in conjunction with, but not limited to, paroxysmal atrial tachyarrhythmias.

All atrial pacing schemes may experience competition between native P waves and paced P waves (also referred to herein as "A waves"), which may induce atrial arrhythmias. In addition, ventricular pacing may combine with retrograde atrioventricular conduction and cause a P wave, which in turn may compete with a native and/or paced P wave. A variety of issues may arise when competition exists between native P waves, retrograde P waves and/or paced P waves. The terms "fusion", "pseudofusion", and "pseudopseudofusion" are typically used to characterize competition between waves.

Fusion is typically characterized by a wave complex formed by depolarization of the myocardium initiated by both a non-native stimulus and a native stimulus. Pseudofusion is typically characterized by a wave complex formed by depolarization of the myocardium initiated by a native stimulus; however, a non-native stimulus, that does not contribute to depolarization, is present that distorts the wave complex. Pseudopseudofusion is typically characterized by an electrocardiographic superimposition of an atrial stimulus on a native QRS complex. In pseudopseudofusion, the atrial stimulus does not contribute to the ventricular activation, which produces the QRS complex. A pseudopseudofusion beat is an artifact of the electrocardiographic recording. Pseudopseudofusion beats occur only in dual chamber pacing schemes and are most common in DVI pacing, but also occur in any atrial pacing mode including AAI, DDI and DDD.

Various fusion, pseudofusion, and/or pseudopseudofusion scenarios may cause a pacing device to waste power. In particular, fusion and pseudofusion may cause a pacing device to deliver a stimulus where native activity would suffice. A pseudopseudofusion beat may well capture in the atrium but as the ventricle is being simultaneously depolarized, it does not contribute to ventricular filling but it may prevent retrograde conduction from occurring. In addition, in a pacing scheme that implements a ventricular autocapture algorithm to set a ventricular stimulus power level, fusion and/or pseudofusion may result in a determination of non-capture, which, in turn, may cause the algorithm to set too high of a ventricular stimulus power level. To minimize the risk of setting an inappropriate power level, various ventricular autocapture algorithms rely on some degree of fusion and/or pseudofusion detection (e.g., fusion by inference). For example, if non-capture is diagnosed following a primary stimulus pulse, then a back-up pulse is delivered and, on the next cycle, the AV delay (or PV delay) is extended (e.g., by approximately 100 ms). Finally, an inference is made that the diagnosed loss of capture is due to fusion if a native R wave is detected within this extended AV delay.

While autocapture algorithms that account for fusion and/or pseudofusion exist for ventricular pacing, they are generally limited. Further, algorithms that account for fusion, pseudofusion and/or other competitive scenarios do not exist for atrial pacing. The lack of such atrial autocapture algorithms are, in part, due to the difficulty in detecting competitive atrial wave behavior. Thus, a need exists for methods and/or devices to detect and/or minimize competitive atrial wave behavior (e.g., caused by native, paced and/or retrograde stimuli). Various exemplary methods and/or devices are described below which may address this need and/or other needs.

SUMMARY

Exemplary methods and devices for determining whether atrial fusion, atrial pseudofusion and/or atrial native activity have occurred. Various methods and/or devices are suitable for use with atrial autocapture. An exemplary method uses ventricular sensing to sense ventricular activity responsive to a native and/or an applied atrial event. Another exemplary method uses such sensed information and/or other information to form AV conduction templates, set sensing windows, etc., which are optionally useful in diagnosing atrial fusion, atrial pseudofusion, and/or native atrial activity.

Various exemplary devices for performing such exemplary methods are also disclosed herein along with a variety of other exemplary methods and/or devices. In general, the various devices and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
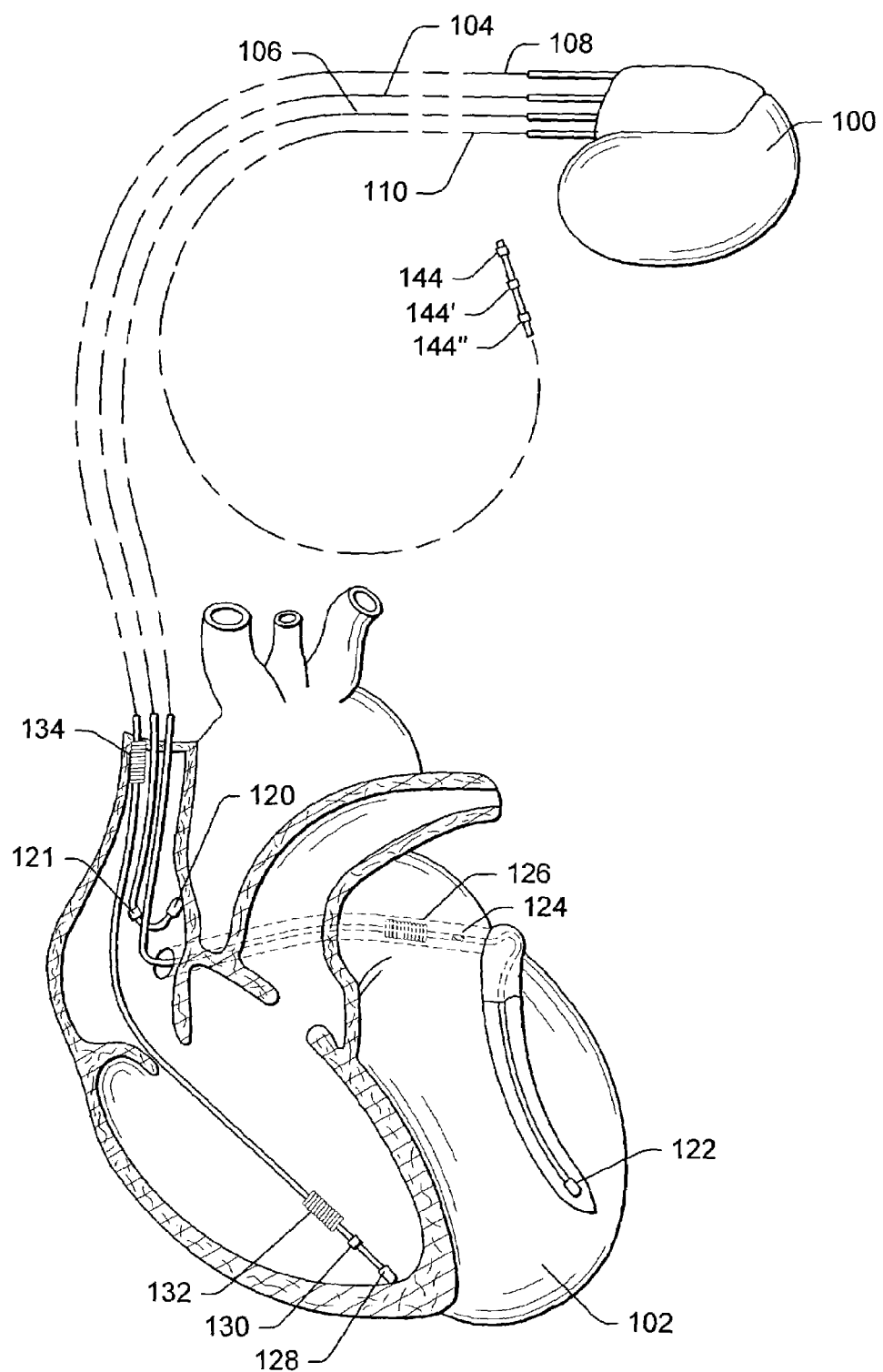
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves and/or detection of other physiologic signals that may be used by the implanted system to modify the pacing parameters. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
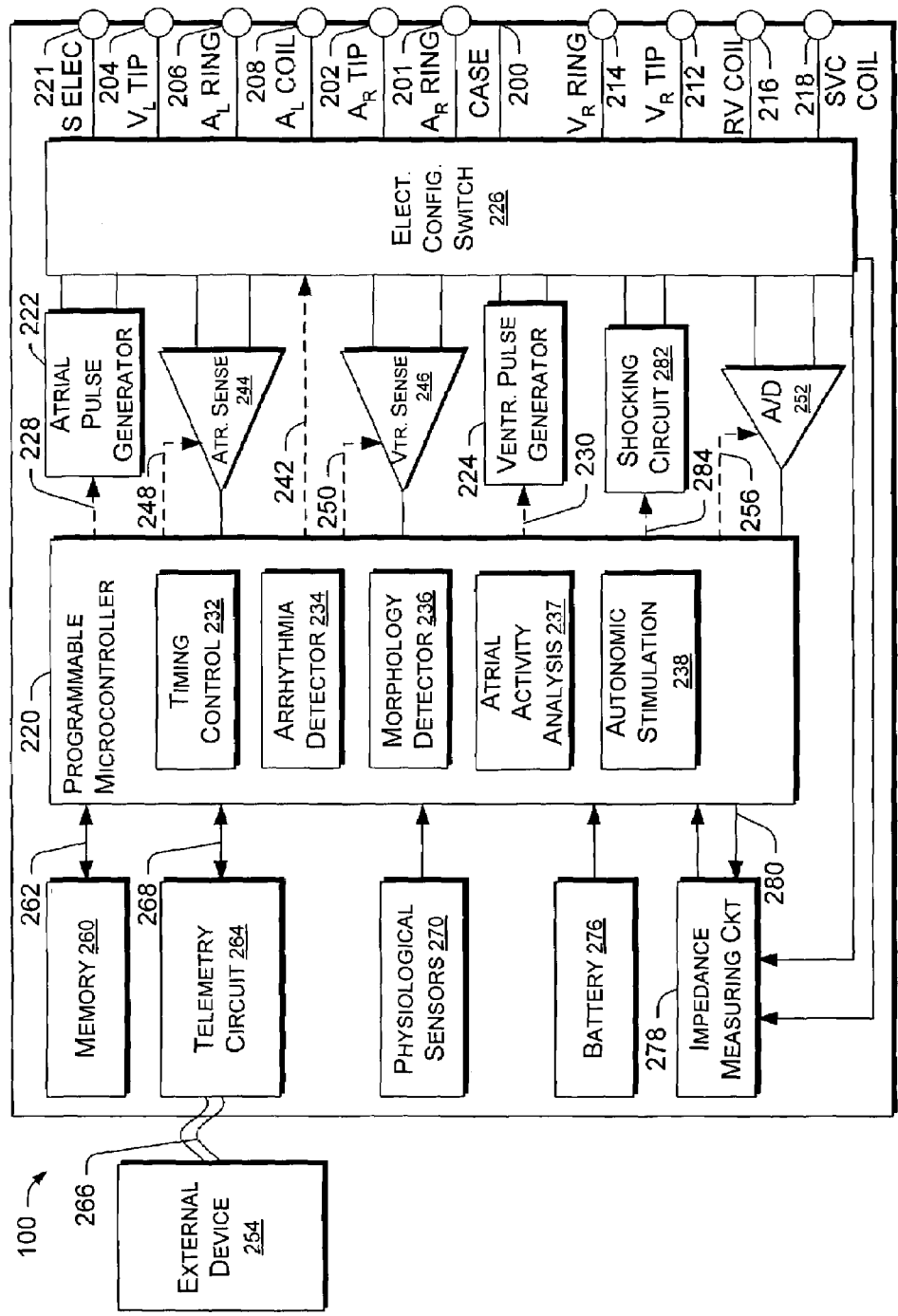
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A—A) delay, or interventricular conduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity. For example, the atrial activity analysis module 237 optionally implements one or more of the exemplary methods described below.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device-100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu$A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythm

Figure 3:
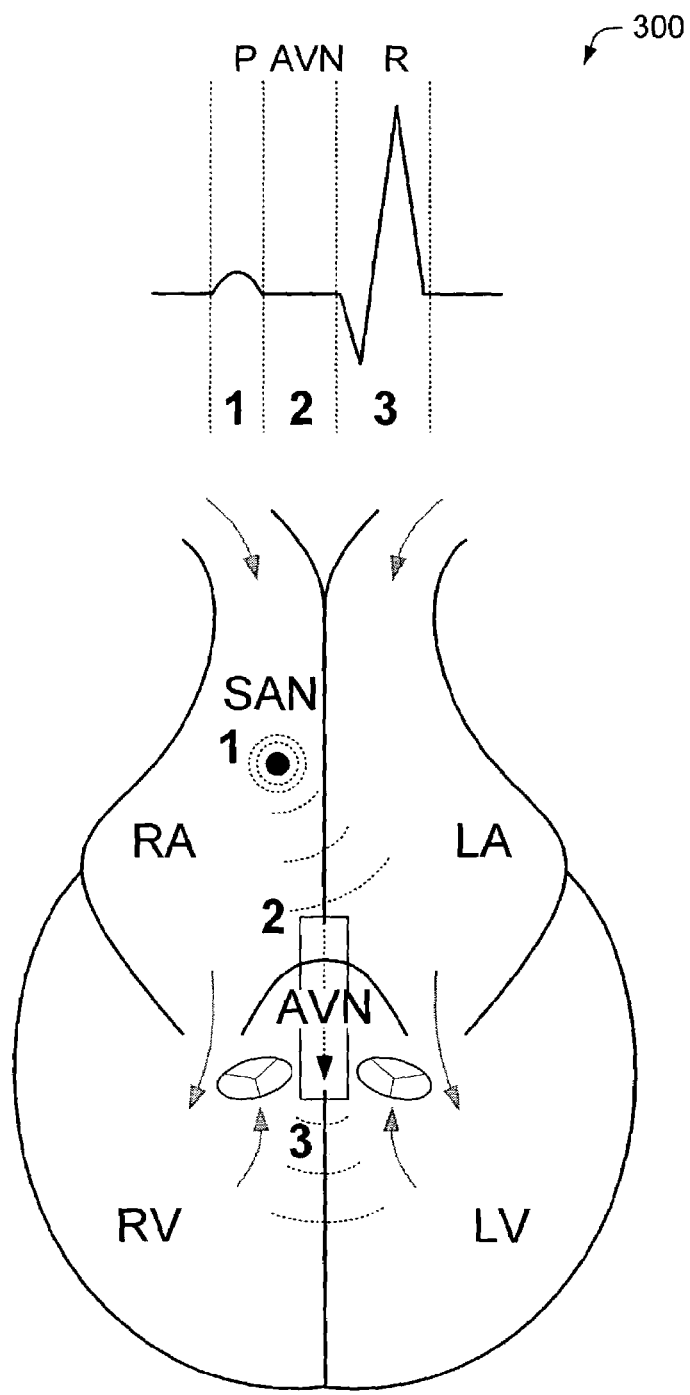
FIG. 3 is an approximate anatomical diagram of a heart and a waveform or ECG wherein the waveform includes a P wave and an R wave.

Referring to FIG. 3, an approximate anatomical diagram of a heart and a PR waveform 300 are shown. Action potentials propagating through a normal heart are labeled as follows: 1, associated with the sinoatrial node (SAN) and the atria; 2, associated with the atrioventricular node and/or atrioventricular bundle (AVN); and 3, associated with the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes ventricular contraction. Thus, in a normal heart, ventricular rhythm relies on conduction of action potentials through the AV node and AV bundle (collectively referred to as the AV node or AVN).

An electrocardiogram (ECG) of normal heart activity (e.g., polarization, depolarization, etc.) typically shows atrial depolarization as a "P wave" and ventricular depolarization as an "R wave", or QRS complex. The time span between a P wave and an R wave typically depends on AVN conduction and/or heart rate (e.g., rate of SAN).

Figure 4:
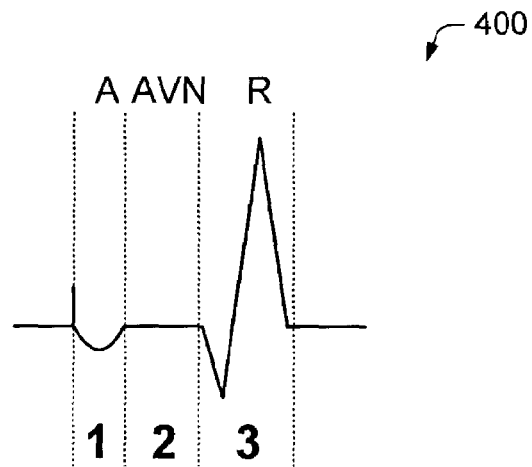
FIG. 4 is an approximate anatomical diagram of a heart and a waveform or ECG wherein the waveform includes an A wave and an R wave.
Figure 4:
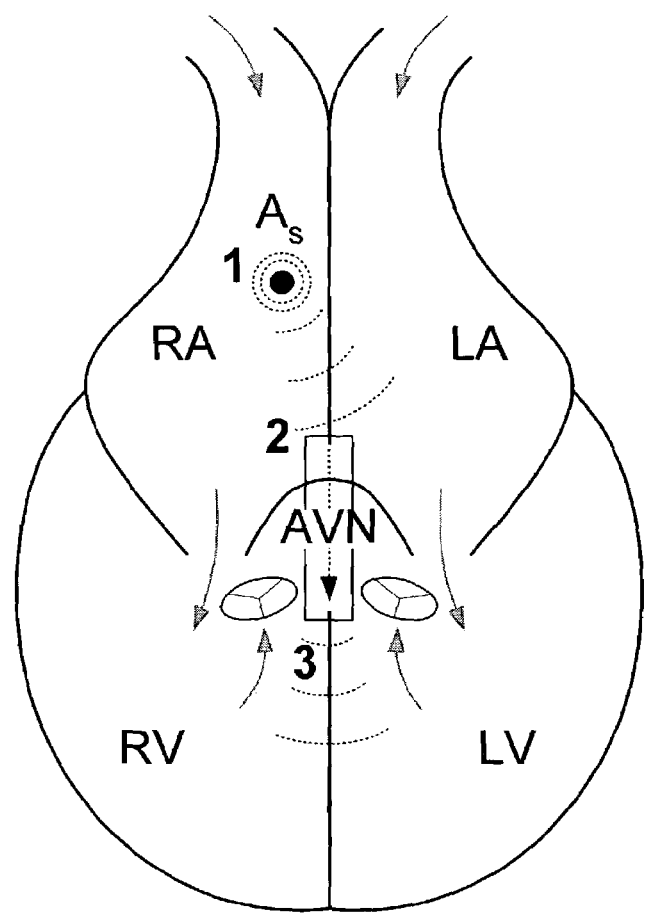

Referring to FIG. 4, an approximate anatomical diagram of a heart, fitted with an atrial pacing device, and an AR waveform 400 are shown. Action potentials propagating through the heart are labeled as follows: 1, associated with a paced atrial stimulus and the atria; 2, associated with the atrioventricular node and/or atrioventricular bundle (AVN); and 3, associated with the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes ventricular contraction. Thus, in this particular atrial paced heart, ventricular rhythm relies on conduction of action potentials through the AV node and AV bundle (collectively referred to as the AV node or AVN).

An electrocardiogram (ECG) of atrial paced heart activity (e.g., polarization, depolarization, etc.) typically shows atrial depolarization as an "A wave" and ventricular depolarization as an "R wave", or QRS complex. The time span between an A wave and an R wave typically depends on AVN conduction and/or heart rate (e.g., rate of atrial pacing, $A_s$).

Thus, in the exemplary hearts and waveforms of FIGS. 3 and 4, ventricular function depends on AVN conduction. The AV node is a small subendocardial structure within the interatrial septum, anterior and superior to the coronary sinus, located at the convergence of specialized conduction tracts that course through the atria. The AV node has extensive autonomic innervation and an abundant blood supply from the large AV nodal artery, which is a branch of the right coronary artery in approximately 90 percent of the population, and from septal branches of the left anterior descending coronary artery. The AV node forms part of the only "normal" electrical connection between atria and ventricles. While various conduction sub- or accessory pathways may exist in the AV node or AV nodal region, the AV node is known to transmit impulses slowly via at least one pathway, e.g., requiring approximately 60 ms to approximately 130 ms to traverse about 1 cm of node tissue. In general, slowing of an impulse by AV nodal tissue protects the ventricles by typically not allowing all impulses through, which, in turn, prevents the ventricles from racing in response to a rapid atrial rhythm. The AV nodal tissue also provides time for atrial contraction to occur to facilitate ventricular filling before ventricular contraction begins. Under some circumstances, the AV node blocks all impulses to the ventricles, which may result in a clinical condition requiring permanent pacing for management. Further, radiofrequency ablation of the AV node can also block all impulses to the ventricles. This is an intentional interventional procedure suited to treatment of recurrent atrial tachyarrhythmias where the ventricular response to those arrhythmias cannot be managed through use of other techniques.

En route to the ventricles, action potentials pass via specialized conduction fibers (right bundle branch, left bundle branch, left anterior superior fascicle, left posterior inferior fascicle) ending in Purkinje fibers. The AV node merges in to the Bundle of His (His Bundle) and these fibers then separate into the ventricular specialized conduction system (bundle branches). Blood supplies the AV bundle from the AV nodal artery and septal branches of the left anterior descending artery. The AV bundle has significant autonomic innervation and is somewhat insulated within a collagenous skeleton. Destruction of the AV bundle, for example, through ablation, may also block all impulses to the ventricles.

While ablation of a patient's AV node and/or AV bundle (e.g., AVN) has been shown to block unwanted conduction of action potentials to the ventricles, these procedures are irreversible; however, methods and/or devices exist to slow and/or block action potentials in a reversible manner (see, e.g., copending U.S. Provisional Patent Application Ser. No. 60/388,623, filed Jun. 12, 2002, titled "Arrhythmia Discrimination), which is incorporated herein by reference). Various exemplary methods and/or exemplary devices disclosed in the above-identified provisional application optionally stimulate nerves to effectively slow and/or block conduction of action potentials through a patient's AV node and/or AV bundle, typically in a reversible manner.

In general, AV conduction blocks are categorized as first-degree, second-degree and third-degree. First-degree block is associated with P wave to R wave prolongation (e.g., greater than approximately 0.2 s) with all P waves followed by QRST. There are three levels of second-degree block. These are classified as type I (Wenckebach), type II or high-grade. Type II involves intermittent blocking of P waves with constant P-R intervals on those conducted complexes. In addition, for a diagnosis of type II, there has to be at least two consecutively conducted P waves. In type I (Wenckebach), there is group beating characterized by a stable atrial rate, a progressive lengthening of the PR interval followed by block or non-conduction of a P wave. This results in a relative pause and the cycle starts over again. The first PR complex of the next cycle has the shortest PR interval. In high grade second degree AV bloc, there is either a 2:1 AV block pattern which has constant P-R intervals on the conducted cycles but every second P wave is blocked. High-grade second degree AV block may also be present when two or more successive P waves are blocked and, in general, the atrial rate exceeds the ventricular rate. Third-degree block is associated with complete dissociation of P waves and QRS complexes and, in general, the atrial rate exceeds the ventricular rate. As described herein, various exemplary methods and/or devices are suitable for use in patients having no AV block and/or first or second degree AV block.

Autonomic Nervous System

As already mentioned, the autonomic nervous system can affect operation of the AV node and/or AV nodal region. The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrioventricular nodal conduction, and ventricular contractile force, also known as contractility or inotropy. Sympathetic efferent postganglionic neurons, when stimulated, generally increase heart rate and increase contractility. Note that contractility is associated with the term "inotropy", heart rate is associated with the term "chronotropy" and conduction velocity is associated with the term "dromotropy".

As already mentioned, the stimulation of parasympathetic nerves can act to decrease heart rate while stimulation of sympathetic nerves can act to increase heart rate. In addition, as noted by Mendelowitz, "Advances in parasympathetic control of heart rate and cardiac function", *News Physiol. Sci.*, 14:155–161 (1999), "when both parasympathetic and sympathetic activity are present, parasympathetic activity generally dominates" and "increases in parasympathetic activity to the heart evoke a bradycardia that is more pronounced when there is a high level of sympathetic firing". Mendelowitz also noted that "the release of acetylcholine from parasympathetic neurons might act presynaptically to inhibit the release of norepinephrine from sympathetic nerve terminals".

Regarding sympathetic stimulation, norepinephrine is released by sympathetic nerves. After its release, norepinephrine acts on the sinoatrial node (SA node) to increase the rate of diastolic depolarization, and thereby increase heart rate, and acts on the atrioventricular node (AV node) to increase the velocity of conduction and diminish the refractory period during which the AV node is unresponsive to stimuli coming from the atrium.

Contractility (or inotropy) refers to the force or strength of cardiac muscle contractions. Stimulation of sympathetic nerves causes active contractility whereas Frank-Starling mechanism causes passive contractility. Active contractility involves norepinephrine, which increases myocardial calcium permeability (or conductance) and hence actin/myosin crossbridge interactions. Other mechanisms may also accompany the increase in calcium permeability.

In general, an increase in ventricular contractility causes an increase stroke volume, which, in turn, can increase cardiac output. Cardiac output (CO) depends on heart rate (HR) and stroke volume (SV) (e.g., CO equals HR times SV). Changes in ventricular contractility alter the rate of force and pressure development by the ventricle and therefore change the rate of ejection (i.e., ejection velocity). For example, an increase in contractility shifts the Frank-Starling curve, which causes a reduction in end-systolic volume and an increase in stroke volume. The increased stroke volume also causes a reduction in ventricular end-diastolic volume (i.e., preload). The end-systolic pressure-volume relationship (ESPVR) may define an inotropic state of the ventricle.

Changes in contractility also produce significant changes in ejection fraction (EF). Increasing contractility leads to an increase in EF, while decreasing contractility decreases EF. Therefore, EF is often used as a clinical index for evaluating the inotropic state of the heart. In heart failure, for example, an associated decrease in contractility leads to a fall in stroke volume as well as an increase in preload, thereby decreasing EF. The increased preload, if it results in a left ventricular end-diastolic pressure greater than approximately 20 mmHg, can lead to pulmonary congestion and edema. Treatment of a patient in heart failure with an inotropic drug (e.g., beta-adrenoceptor agonist or digoxin) shifts the depressed Frank-Starling curve up and to the left, thereby increasing stroke volume, decreasing preload, and increasing EF.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Another term used to describe cardiac operation is "cardiac workload", which is sometimes defined as the product of systolic blood pressure and heart rate. In general, an increase in inotropy, chronotropy and/or dromotropy result in an increase in cardiac workload. Further, sympathetic activity is likely to increase cardiac workload whereas parasympathetic activity is likely to decrease cardiac workload.

Atrial Paced and/or Native Waveforms

Figure 5:
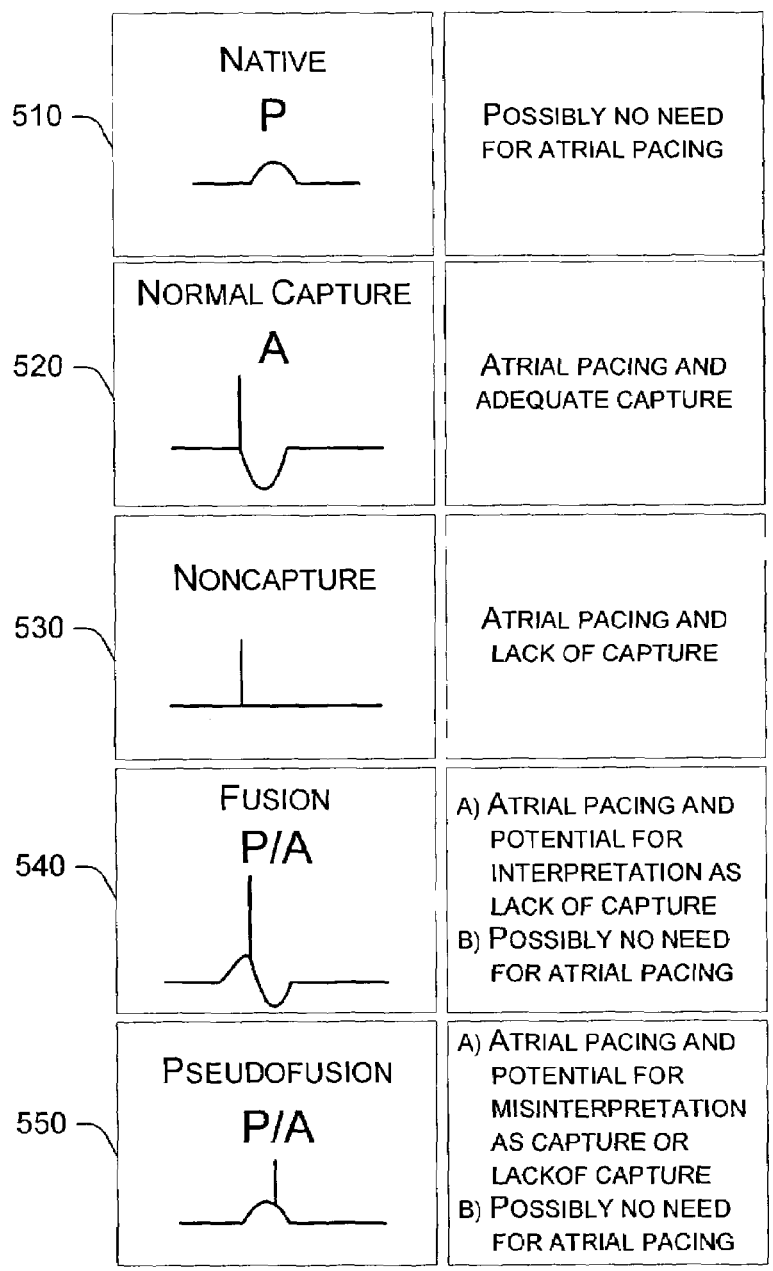
FIG. 5 is a diagram of various exemplary atrial waveforms including native (P wave), capture (A wave), noncapture (with atrial stimulus), atrial fusion (P wave and A wave complex) and atrial pseudofusion (P wave with atrial stimulus).

Referring to FIG. 5, various exemplary atrial waveforms 500 are shown. As discussed herein, an atrial waveform caused by an atrial stimulus is generally referred to as an A wave while an atrial waveform caused by a native stimulus (e.g., SAN) is generally referred to as a P wave. A native P wave 510 (e.g., per an ECG) may indicate that a patient does not need atrial pacing. However, if the native rate (e.g., as measured from P wave to P wave), falls below a desirable rate (e.g., exceeds a given interval), then atrial pacing may be indicated. An A wave 520 (e.g., per an ECG) indicates that an applied atrial stimulus was delivered at a time when the atrial myocardium was capable of being stimulated and had sufficient energy to "capture" atrial tissue. In comparison to the A wave 520, the noncapture waveform 530, indicates that the applied atrial stimulus did not have sufficient energy to capture atrial tissue or was delivered at a time when the atrial tissue was physiologically refractory. The last two waveforms 540, 550 exhibit atrial "fusion" and atrial "pseudofusion", respectively.

As mentioned in the Background section, fusion is typically characterized by a wave complex formed by depolarization of the myocardium initiated by both a non-native stimulus and a native stimulus. Thus, atrial fusion is characterized by a wave complex (e.g., the waveform 540) initiated by a native stimulus (e.g., from the SAN) and a paced atrial stimulus. As mentioned in the Background section, pseudofusion is typically characterized by a wave complex formed by depolarization of the myocardium initiated by a native stimulus; however, a non-native stimulus, that does not significantly contribute to depolarization, is present that distorts the wave complex. Thus, atrial pseudofusion is characterized by a wave complex (e.g., the waveform 550) initiated by a native stimulus and distorted by a paced atrial stimulus.

Pacing devices that implement atrial autocapture may misinterpret fusion and/or pseudofusion waveforms as noncapture or loss of capture. Further, a pacing device may not need to implement atrial pacing if a native stimulus is present. Again, in both fusion and pseudofusion (e.g., the waveforms 540, 550), native atrial activity is present.

Dual Chamber Pacing Devices

Dual chamber pacing devices have an ability to pace and/or sense in one or more atria and one or more ventricles. In general, atrial events occur on an atrial channel and ventricular events occur on a ventricular channel. In dual chamber pacing devices, a variety of intervals or timing periods exist. For example, a "basic interval" is typically defined as the time interval between two consecutive paced events in the same chamber without an intervening sensed event. A "blanking period" is a typically a time interval following a stimulus wherein sensing does not occur. For example, an atrial stimulus may disable ventricular channel sensing for approximately 25 milliseconds to prevent inadvertent sensing of the atrial stimulus by the ventricular channel, thereby preventing inappropriate inhibition of ventricular output. In general, a blanking period aims to minimize cross-talk between channels. For example, an atrial blanking period termed a post-ventricular atrial blanking period (PVAB) is associated with a paced or sensed ventricular event that prevents detection of a ventricular event on an atrial channel.

The interval between either an atrial sensed or an atrial stimulus and the delivery of a ventricular stimulus is termed the PV interval or AV interval (PVI, AVI) respectively. Commonly, the term AV interval is used interchangeably to refer to both paced and sensed AV intervals. The AV interval is usually programmed to approximately 150 milliseconds to approximately 220 milliseconds and may be lengthened to allow for native AV nodal conduction in cases of P wave to R wave intervals (PRI). Even longer AV delays may be programmed if intrinsic conduction is desired but the conduction time between the atria and ventricles is delayed. During the AV interval, the atrial channel is typically refractory to any sensed events and thus constitutes a portion of the atrial refractory period. Another interval used herein is referred to as the A wave/atrial stimulus to sensed R wave interval (ARI). The ARI is commonly a subset of the AVI. ARI, however, is dependent on native conduction and while possibly adjustable via AV nodal control, is not a programmable interval in the pacemaker.

The "postventricular atrial refractory period" (PVARP) is a period of atrial refractoriness that extends beyond the delivery of a ventricular stimulus or beyond a ventricular sensed event. The PVARP helps to prevent pacemaker-mediated tachycardia by ignoring retrogradely conducted atrial impulses. The "total atrial refractory period" (TARP) is the sum of the AVI and the PVARP. During this period, native atrial events are not sensed. The "atrial escape interval" (AEI) is the interval that begins with a ventricular sensed or paced event and ends with an atrial paced event. The lower rate limit (LRL) for a DDD pacing scheme typically equals the AVI plus the AEI when it utilizes ventricular based timing. When the basic timing system utilizes atrial based timing, the AEI is the interval from one atrial or sensed event to the next atrial paced event if the timing system is not reset by a detected native ventricular event occurring between termination of the ventricular refractory period and delivery of the atrial stimulus.

In general, DDI and DDD pacing schemes are distinguishable on the basis of their response to an atrial event sensed during the AEI. In a DDD scheme, any sensed atrial event occurring after the PVARP but before the AEI is completed will be sensed and initiate a PVI unless a spontaneously conducted QRS complex occurs before the PVI can be completed. In a DDI scheme, an atrial event sensed during the AEI causes suppression of the next atrial event due to an inhibitory function but does not alter timing of the ventricular stimulus. If the native P wave does not conduct, the system will deliver a ventricular output at the end of the ventricular escape interval.

Another issue in dual chamber devices is referred to as crosstalk, which most commonly refers to ventricular sensing of far-field atrial stimulus. Depending on the dual chamber pacing scheme, inappropriate sensing of an atrial stimulus on a ventricular channel may cause inhibition of ventricular output and resetting of the atrial escape interval. At worst, in the presence of concomitant AV block, crosstalk can be catastrophic, resulting in ventricular asystole. One approach to minimizing crosstalk involves initiating a ventricular refractory period simultaneous with initiation of a programmed atrial stimulus. However, this approach results in committed DVI pacing. Other approaches involve use of a ventricular blanking period (e.g., typically approximately 12 ms to approximately 125 ms) that disengages the ventricular sense amplifier coincident with the release of the atrial output pulse.

In some pacing devices, a special detection window, known as a crosstalk detection window, follows the ventricular blanking period or other timed or sensed event. In commercial pacing devices, the duration of this special window typically varies from approximately 51 ms to approximately 150 ms. In certain pacing devices, detection of a far-field atrial stimulus on the ventricular channel during the crosstalk detection window may trigger a ventricular stimulus to be delivered at an abbreviated AV interval (sometimes referred to as ventricular safety standby pacing).

As discussed herein, a special detection window on the ventricular channel (or other suitable channel) is implemented and, for example, initiated by an atrial stimulus. This special window has a fixed or a programmable duration and optionally varies depending on pacing rate, AV conduction and/or autonomic tone (e.g., parasympathetic tone and/or sympathetic tone). AV nodal conduction templates optionally assist in determining window duration.

Special Detection Window

Figure 6:
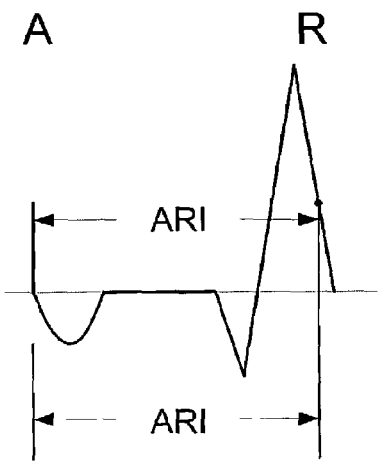
FIG. 6 is a diagram of various exemplary waveforms, including atrial capture, atrial fusion and atrial pseudofusion, and corresponding A wave to R wave intervals (ARI).
Figure 6:
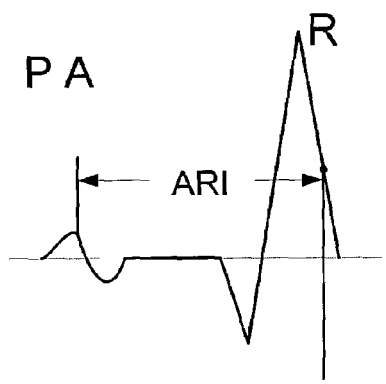
Figure 6:
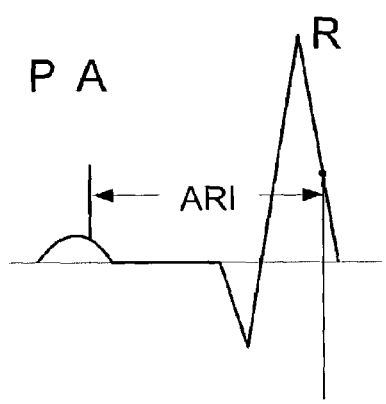

Referring to FIG. 6, exemplary waveforms 600 are shown, which help to understand better various exemplary methods and/or devices that implement a special detection window. An exemplary atrial capture and QRS waveform 610 includes an A wave and a corresponding R wave (e.g., QRS complex). In this waveform 610, atrial capture responsive to the stimulus controls and the interval from the atrial stimulus or onset of the A wave to the sensed R wave is referred to as the AR interval (ARI). This is diagramed schematically with ventricular sensing occurring late within the native QRS complex, as this is a relatively common phenomenon. However, in any individual patient, R wave sensing may occur at any particular time within the QRS complex.

An exemplary atrial fusion and QRS waveform 620 includes a P/A wave complex and a corresponding R wave, for example, initiated by conduction of the P/A wave complex. In this waveform 620, a native depolarization controls and the paced atrial stimulus also causes depolarization that fuses with the native P wave. In this instance, based on the timing of the paced atrial stimulus, the sensed R wave appears earlier than expected with respect to the delivered atrial output pulse.

An exemplary atrial pseudofusion and QRS waveform 630 includes a P wave distorted by a paced atrial stimulus and a corresponding R wave, for example, initiated by conduction of the P wave. In this waveform 630, "A" represents the timing of a paced atrial stimulus that failed to "capture" atrial tissue because the atrial tissue was physiologically refractory. As for the fusion waveform 620, the pseudofusion waveform 630 has an ARI that is shorter than expected because, based on the timing of the paced atrial stimulus, the sensed R wave appears earlier than expected.

A special ventricular channel sensing window may be established on the basis of information contained within these exemplary waveforms and/or timed pacing events. For example, an exemplary ventricular sensing window may account for possible fusion-based and/or pseudofusion-based R wave deviations. In this example, the exemplary ventricular sensing optionally commences at a time sufficient to detect an R wave corresponding to atrial fusion and/or atrial pseudofusion. As described in more detail below, a ventricular detection window may also account for atrial paced rates and/or autonomic tone.

Detection Window Based on Paced Atrial Rate and/or Autonomic Activity

Figure 7:
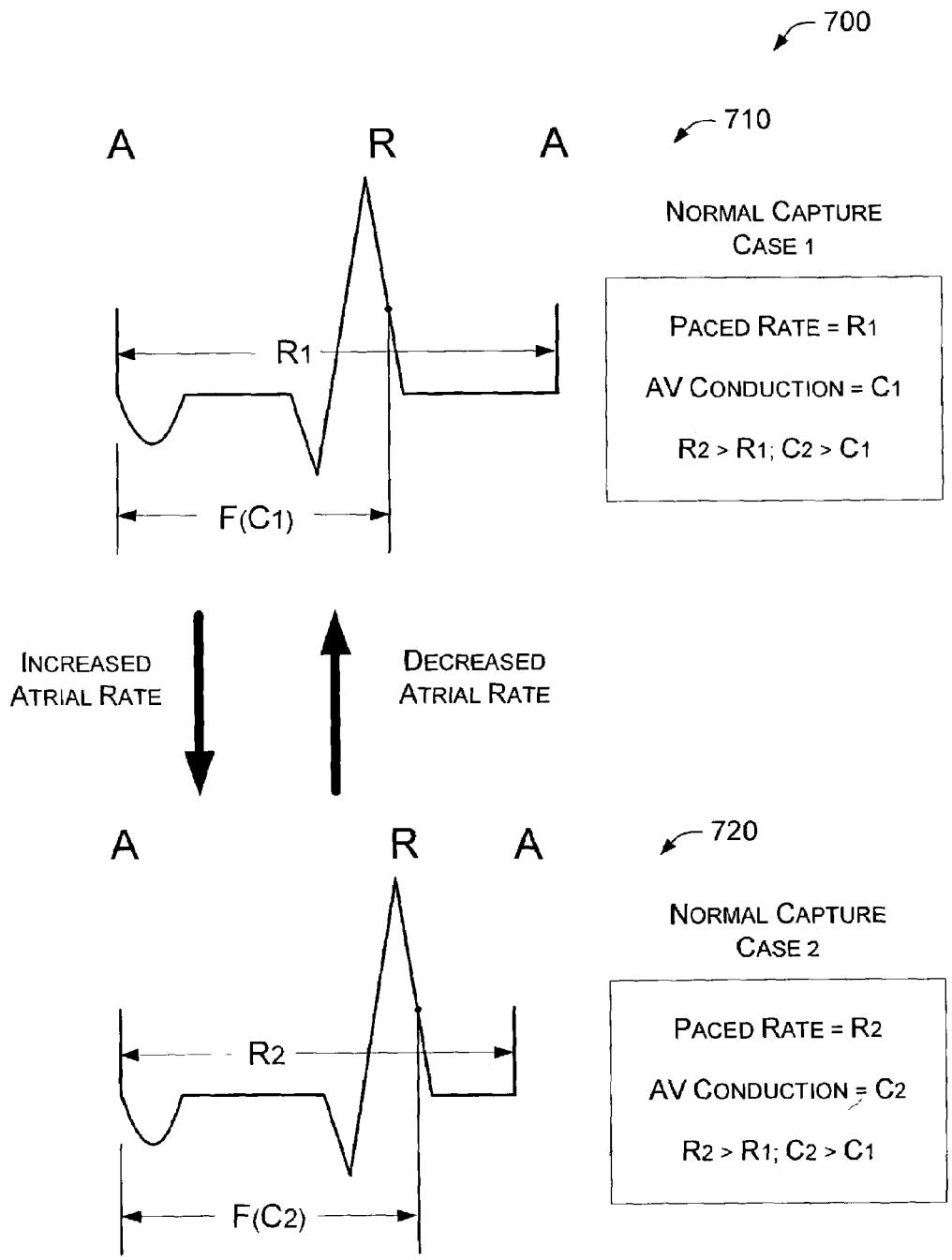
FIG. 7 is a diagram of exemplary waveforms for two atrial pacing rates and corresponding A wave to R wave intervals (ARI) that exhibit conduction differences.

Referring to FIG. 7, two approximate waveforms 710, 720 are shown. The waveform 710 includes an A wave to A wave interval (AAI) and an A wave to R wave interval (ARI) for a paced atrial rate R1 and an AV conduction C1. The ARI is a function of C1 (e.g., a conduction rate in meters per second), as represented by the time interval F(C1) (e.g., a time in seconds). The waveform 720 includes an A wave to A wave interval (AAI) and an A wave to R wave interval (ARI) for a paced atrial rate R2 and an AV conduction C2 (e.g., a conduction rate in meters per second). In this waveform, the ARI is a function of C2, as represented by the time interval F(C2). As shown in the exemplary waveforms 710, 720 of FIG. 7, the paced atrial rate R2 is greater than R1; hence, the AAI for the waveform 720 is less than the AAI for the waveform 710. In addition, the AV conduction C1 (e.g., in m/s) is greater than C2 (e.g., in m/s) and the ARI and F(C2) (e.g., in seconds) for the waveform 720 is greater than the ARI and F(C1) (e.g., in seconds) for the waveform 710. In general, AV conduction rate increases as atrial rate decreases and AV conduction rate decreases as atrial rate increases in a physiologic setting as associated with P waves. In the setting of pacing, particularly in association with rate modulation, if the increase in the atrial paced rate is not balanced with the intrinsic physiologic (autonomic) tone of the patient, the increase in atrial rate may be associated with and increase in the ARI, for example, as represented by the time interval F(C2). If the ARI is sufficiently long, the conducted R wave will not be sensed before a ventricular stimulus will be released at the end of the AVI. An exemplary method for fusion and/or pseudofusion detection optionally accounts for such typical physiologic behavior. For example, a special detection window for an R wave may shift and/or extend to account for an increase in paced atrial rate. Likewise, a special detection window for an R wave may shift and/or initiate sooner for a decrease in paced atrial rate. This can be further refined with supplemental sensors detecting concomitant changes in the physiologic state.

Figure 8:
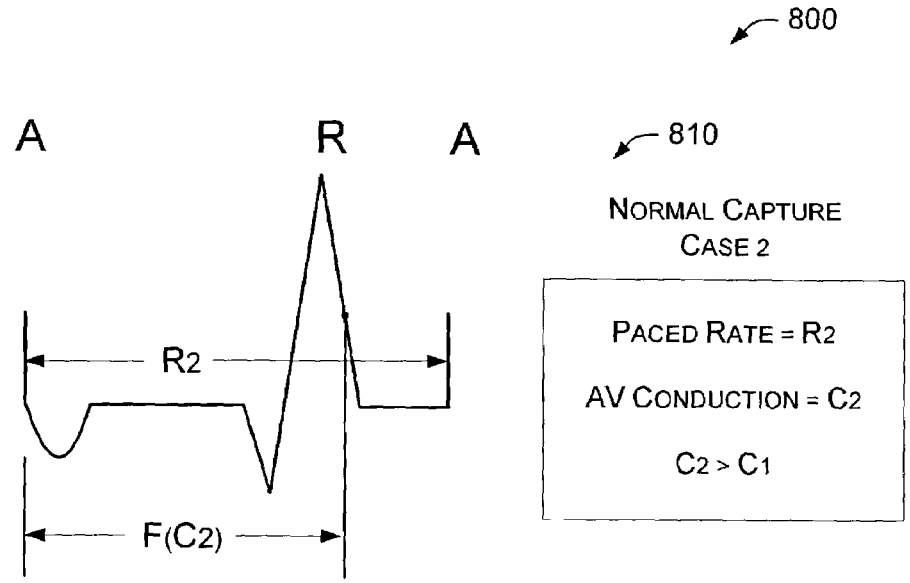
FIG. 8 is a diagram of exemplary waveforms for two levels of autonomic activity and/or autonomic tone and corresponding A wave to R wave intervals (ARI) that exhibit conduction differences.
Figure 8:
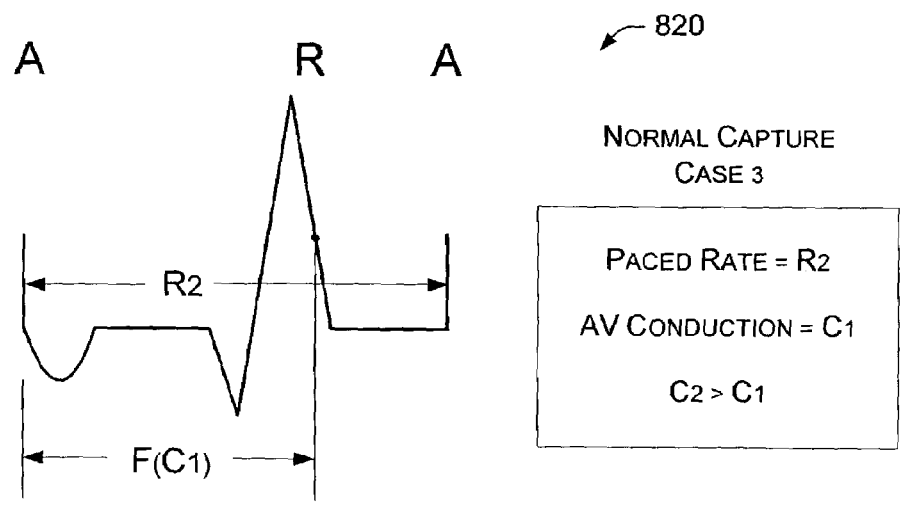

Referring to FIG. 8, two approximate waveforms 810, 820 are shown. The waveform 810 includes an A wave to A wave interval (AAI) and an A wave to R wave interval (ARI) for a paced atrial rate R2 and an AV conduction rate C2 (e.g., in meters per second). The ARI is a function of C2, as represented by the time interval F(C2) (e.g., in seconds). The waveform 820 includes an A wave to A wave interval (AAI) and an A wave to R wave interval (ARI) for a paced atrial rate R2 and an AV conduction rate C1 (e.g., in m/s). In this waveform, the ARI is a function of C1 (e.g., in m/s), as represented by the time interval F(C1) (e.g., in seconds). As shown in the exemplary waveforms 810, 820 of FIG. 8, the AAI for the waveform 820 approximately equals the AAI for the waveform 810. However, the AV conduction rate C1 (e.g., in m/s) is greater than the rate C2 (e.g., in m/s) and the ARI or F(C2) (e.g., in seconds) for the waveform 810 is greater than the ARI or F(C1) (e.g., in seconds) for the waveform 820. In general, AV conduction rate (e.g., in m/s) slows for an increase in parasympathetic activity while AV conduction rate (e.g., in m/s) becomes more rapid or improves for an increase in sympathetic activity. An exemplary method for fusion and/or pseudofusion detection optionally accounts for such typical physiologic behavior. For example, a special detection window for an R wave may shift and/or extend to account for an increase in parasympathetic activity and/or a decrease in sympathetic activity, both of which may slow AV conduction. Likewise, a special detection window for an R wave may shift and/or initiate sooner for a decrease in parasympathetic activity and/or an increase in sympathetic activity, both of which may speed or improve AV conduction.

Figure 9:
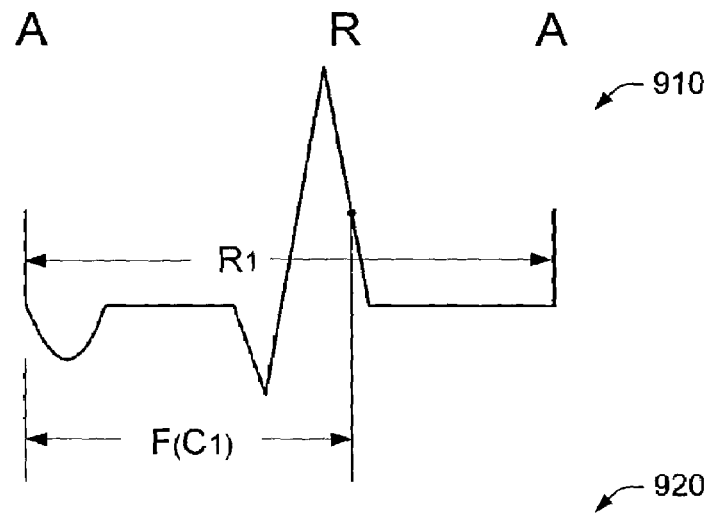
FIG. 9 is a diagram of an exemplary waveform and a corresponding atrial sensing channel and a corresponding ventricular sensing channel wherein arrows indicate possible trends for changes in atrial rate and/or autonomic activity and/or autonomic tone.
Figure 9:

Referring to FIG. 9, an exemplary waveform and exemplary sensing channels 900 are shown. The sensing channels 920 include an atrial evoked response sensing channel 924 and a ventricular sensing channel 928. The atrial evoked response sensing channel 924 includes an atrial evoked response sensing window (AERW) that commences approximately following an atrial stimulus. The ventricular sensing channel 928 includes an R wave detection window (RDW) or special detection window for sensing an R wave.

Two arrows are shown below the RDW, a right pointing arrow corresponds to shifting (e.g., moving) and/or lengthening (e.g., extending) the RDW to the right (i.e., later times). This is appropriate when AV conduction slows, which will delay arrival of the atrial depolarization in the ventricles. For example, an increase in parasympathetic activity and/or a decrease in sympathetic activity will typically slow AV conduction. As AV conduction slows, ventricular depolarization will occur at later times.

The left pointing arrow corresponds to shifting (e.g., moving) and/or lengthening (e.g., extending) the RDW to the left (i.e., earlier times) for a decrease in parasympathetic activity (e.g., acceleration of spontaneous diastolic depolarization and of AV conduction) and/or a increase in sympathetic activity (e.g., acceleration of both spontaneous diastolic depolarization and AV conduction).

AV conduction may also change in response to changes in atrial rate. For example, an increase in atrial rate, when paced, may be associated with slowing of conduction through the AV node if the degree of rate increase exceeds the physiologic state. However, if the atrial rate increases on a physiologic basis as due to intrinsic atrial activity, this is usually due to increased sympathetic activity with the positive dromotropic effect and shortening of the PR interval due to improved AV conduction. For this latter case, shifting and/or lengthening the RDW window to the left (i.e., earlier times) may be appropriate. In addition, decreases in atrial rate due to either the sensor or associated with intrinsic slowing of the native atrial focus is most commonly associated with an increase in parasympathetic activity or a decrease in sympathetic activity. In such instances, extending and/or shifting the RDW to the right (i.e., later times) may be appropriate. If the underlying reasons for a change in atrial rate are known, or assumed, then a change in the RDW may suitably account for changes in AV conduction.

Accordingly, an RDW may lengthen, shift and/or commence earlier in time to account for a variety of physiologic changes (e.g., rate, autonomic activity, etc.).

Exemplary Initial "Noncapture" Scenario

Figure 10:
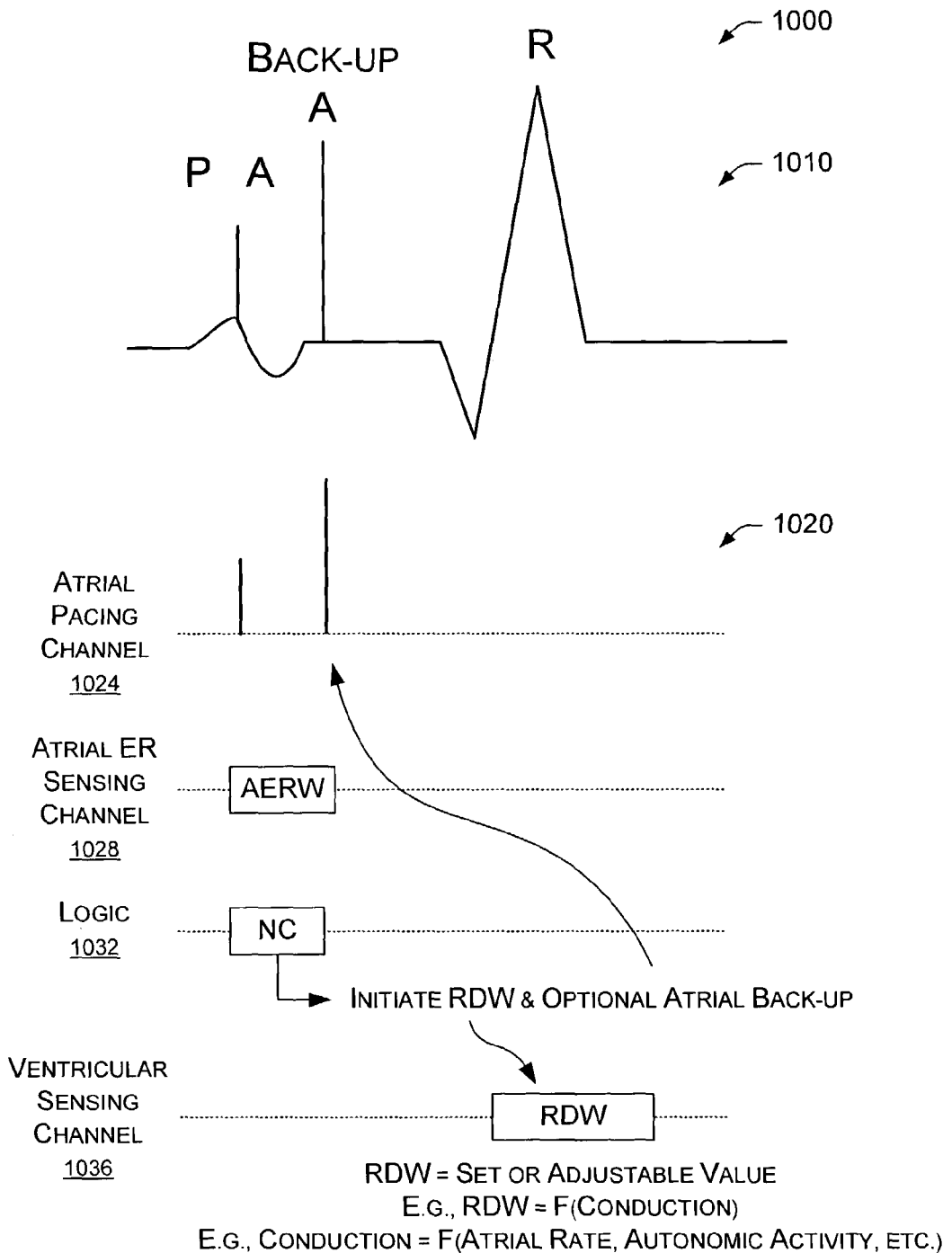
FIG. 10 is a diagram of an exemplary waveform for an initial atrial "noncapture" scenario and corresponding atrial and ventricular channels and logic.

Referring to FIG. 10, an exemplary scenario 1000 that includes an exemplary waveform 1010 and exemplary channels and logic 1020 are shown. The exemplary waveform 1010 includes both atrial and ventricular events including a P/A fusion wave, a back-up A stimulus and an R wave. The exemplary channels and logic 1020 include an atrial pacing channel 1024, an atrial evoked response sensing channel 1028, a logic line 1032, and a ventricular sensing channel 1036. The atrial pacing channel 1024 includes an initial atrial stimulus and a larger magnitude back-up atrial stimulus. The atrial evoked response (ER) sensing channel 1028 includes an atrial evoked response sensing window (AERW) that commences approximately following the initial atrial stimulus. The logic line 1032 includes logic for making an initial determination as to whether the initial atrial stimulus resulted in atrial capture. As indicated by the logic line 1032, in this particular scenario 1000, the logic made an initial determination that atrial capture did not occur (e.g., noncapture or NC). According to this scenario 1000, an initial determination of noncapture causes initiation or implementation of an R wave detection window on the ventricular sensing channel 1036 and optionally an atrial back-up stimulus on the atrial pacing channel 1024 (as shown). Suitable logic implements a set RDW and/or determines an appropriate RDW, for example, according to AV conduction, etc. As described in further detail below, an RDW is optionally set and/or determined on the basis of trials, which may be used to derive one or more "templates", data tables, parameters, equations, etc.

Referring again to FIG. 10, according to the exemplary waveform 1010, an R wave coincides with the RDW. In this instance, suitable logic would indicate that the initial determination of noncapture should be more accurately characterized as atrial fusion and/or atrial pseudofusion. Further, the presence of atrial fusion and/or atrial pseudofusion may lead to a conclusion that native atrial activity was present. Yet further, native atrial activity may indicate that atrial pacing is not necessary. Termination of atrial pacing in response to such circumstances may help conserve power and/or extend life of a power supply. It has also been reported that the native atrial depolarization is hemodynamically superior to a paced atrial depolarization (e.g., evoked response, capture). Allowing for native atrial activity may therefore also improve the hemodynamic state of the patient. Thus, exemplary algorithms optionally promote native atrial depolarization to improve hemodynamics.

Exemplary Method for Determining Information Based on Rate

Figure 11:
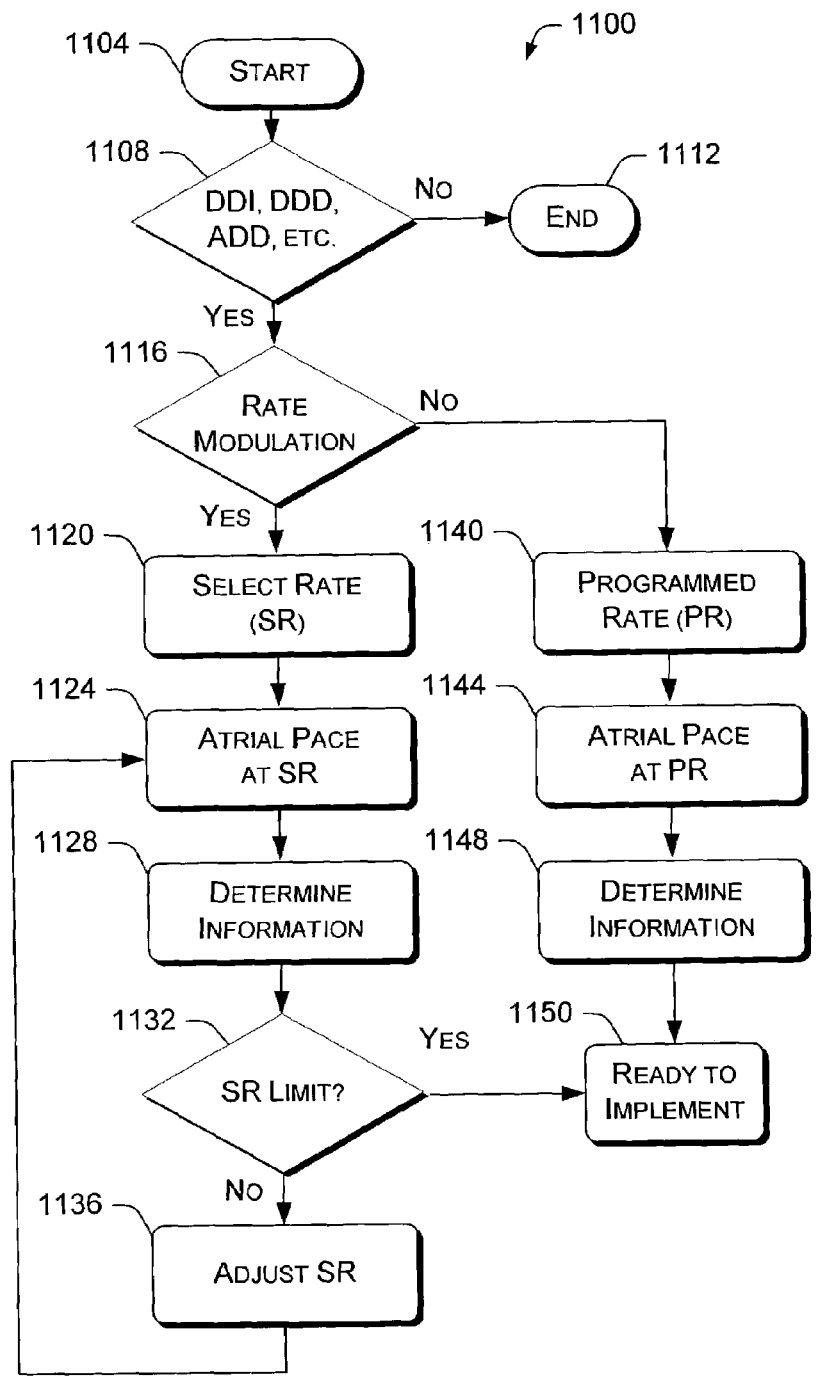
FIG. 11 is a block diagram of an exemplary method for determining information germane to, for example, R wave sensing on a ventricular sensing channel in response to a paced atrial stimulus for one or more atrial rates.

Referring to FIG. 11, an exemplary method 1100 for determining information (e.g., RDW, template, timing, etc.) based on atrial rate is shown. The method 1100 commences in a start block 1104. A decision block 1108 follows the start block 1104 wherein the method 1100 determines whether DDI, DDD or another pacing scheme is operable. An example of another pacing scheme is ADD, which may be optionally implemented in single chamber atrial pacing system but where there could also be ventricular sensing (see, e.g., Levine, P. A., "Confirmation of atrial capture and determination of atrial capture thresholds in DDD pacing systems", *Clinical Progress in Pacing and Electrophysiology*, 2: 465–473 (1984). If the decision block 1108 determines, for example, that a dual-chamber atrial pacing mode such as DDI or DDD pacing schemes, which are most common, are not operable, then the method 1100 terminates in an end block 1112. In the instance that an atrial pacing mode (e.g. DDI, DDD, ADD, etc.) is operable, then the method 1100 continues in another decision block 1116 wherein the method 1100 determines whether rate modulation is operable (e.g., DDIR, DDDR, ADDR). If the decision block 1116 determines that rate modulation is operable, then the method 1100 continues in a select rate (SR) block 1120; however, if the decision block 1116 determines that rate modulation is not operable, then a programmed rate (PR) block 1140 follows.

For DDIR and/or DDDR pacing schemes, the method 1100 selects a rate (SR) in the select rate block 1120. An atrial pace block 1124 follows wherein pacing at the selected atrial rate (SR) commences. Next, the method 1100 determines information germane to AV conduction and/or detection of an R wave on a ventricular sensing channel (or other suitable channel) that corresponds to an atrial stimulus. The method 1100 optionally collects information after multiple atrial stimuli at the atrial rate SR. Such information is optionally suitable for use in forming a template. According to the exemplary method 1100, after the determination block 1128, yet another decision block 1132 decides whether an atrial pacing rate limit has been reached. For example, a first SR may correspond to a lower atrial pacing limit, a second SR may correspond to the first SR plus 10 bpm, and so on until an upper atrial pacing limit is reached and/or exceeded. Indeed, as shown, if the decision block 1132 decides that an SR limit has not been reached and/or exceeded, then the method 1100, for rate modulation (e.g., DDIR, DDDR), continues at the change rate block 1136. In the instance that a SR limit is reached and/or exceeded, then the method 1100 continues in a ready block 1150 wherein the collected information is ready to implement in an exemplary method having a special detection window, etc.

In an alternative example, a first SR may correspond to an upper atrial pacing limit and a second SR may correspond to the first SR minus 10 bpm (or a percentage, etc.) and so on until a lower atrial pacing limit is reached and/or exceeded. This approach may avoid inducement of AV block (e.g., first or higher degree), which may occur through use of an atrial rate that is too rapid for the physiologic state. Use of a lower rate or rates may allow for more AV nodal recovery time and improved AV conduction.

Further, progressively increasing the rate in accord with SR may induce at least first degree AV block as the atrial rate is too rapid for the physiologic state. Hence, in an alternative implementation, the SR allowed to be lower rather than higher. The lower rate gives the AV node more time to recover on a physiologic basis allowing for improved conduction. In a manner analogous to ventricular AutoCapture with fusion avoidance, the lower rate will allow the native atrial activity, if this was fusion, to be manifest and may even allow it to be sensed during the atrial alert window.

As already mentioned, in the instance that the decision block 1116 determines that rate modulation is not operable, the method 1100 proceeds to the programmed rate (PR) block 1140. An atrial pace block 1144 follows wherein pacing at the programmed atrial rate (PR) commences. Next, the method 1100 determines information germane to AV conduction and/or detection of an R wave on a ventricular sensing channel (or other suitable channel) that corresponds to an atrial stimulus. The method 1100 optionally collects information after multiple atrial stimuli at the atrial rate SR. Such information is optionally suitable for use in forming a template. After the determination block 1148, the method 1100 continues in a ready block 1150 wherein the collected information is ready to implement in an exemplary method having a special detection window, etc.

According to the exemplary method 1100, information is collected for a programmed rate and/or one or more selected rates. A pacing device optionally uses such information to help determine whether an atrial stimulus resulted in atrial fusion and/or atrial pseudofusion.

Exemplary Method for Determining Information Based on Autonomic Activity

Figure 12:
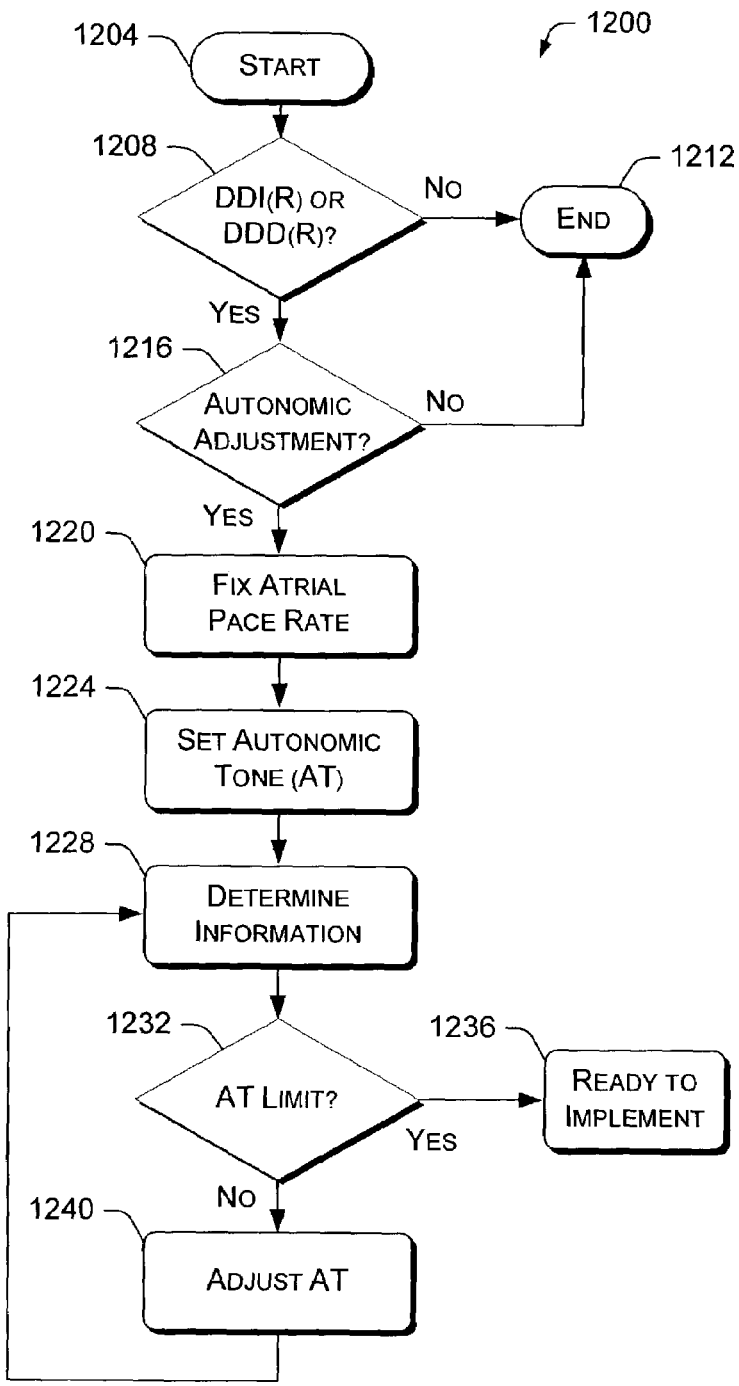
FIG. 12 is a block diagram of an exemplary method for determining information germane to, for example, R wave sensing on a ventricular sensing channel in response to a paced atrial stimulus for one or more levels of autonomic activity and/or autonomic tone.

Referring to FIG. 12, an exemplary method 1200 for determining information (e.g., RDW, template, timing, etc.) based on autonomic state and/or autonomic activity is shown. The method 1200 commences in a start block 1204. A decision block 1208 follows the start block 1204 wherein the method 1200 determines whether DDI(R), DDD(R) or another pacing scheme is operable. If the decision block 1208 determines that DDI(R) or DDD(R) pacing schemes are not operable, then the method 1200 terminates in an end block 1212. In the instance that a DDI(R) or DDD(R) pacing is operable, then the method 1200 continues in another decision block 1216 wherein the method 1200 determines whether autonomic adjustment is operable (e.g., stimulus of autonomic nerves, etc.). If the decision block 1216 determines that autonomic adjustment is not operable, then the method 1200 terminates in the end block 1212. However, if autonomic adjustment is operable, then the method continues in a set atrial pacing rate block 1220. In this exemplary method 1200, atrial pacing rate is held constant while autonomic activity and/or tone is adjusted. Accordingly, information is collected as a function of autonomic activity and/or tone for one or more fixed atrial pacing rates.

In the instance that autonomic adjustment is operable per the decision block 1216, the method 1200 then, in a set block 1224, sets autonomic activity and/or tone. Next, the method 1200 determines information germane to AV conduction and/or detection of an R wave on a ventricular sensing channel (or other suitable channel) that corresponds to an atrial stimulus (e.g., per the fixed atrial pacing rate). The method 1200 optionally collects information after multiple atrial stimuli at the fixed atrial pacing rate. Such information is optionally suitable for use in forming a template. According to the exemplary method 1200, after the determination block 1228, yet another decision block 1232 decides whether an autonomic adjustment limit has been reached. For example, a first autonomic adjustment may correspond to a lower parasympathetic stimulation limit, a second adjustment may correspond to 110% of the first adjustment, and so on until an upper autonomic adjustment limit is reached and/or exceeded. Indeed, as shown, if the decision block 1232 decides that an autonomic adjustment limit has not been reached and/or exceeded, then the method 1200 continues at the adjust autonomic activity and/or tone block 1240. In the instance that a limit is reached and/or exceeded, then the method 1200 continues in a ready block 1236 wherein the collected information is ready to implement in an exemplary method having a special detection window, etc.

While the exemplary method 1100 of FIG. 11 relies on adjustment of rate, if possible or suitable, the exemplary method 1200 of FIG. 12 relies on adjustment of autonomic activity and/or tone. Of course hybrid methods are also possible.

Exemplary Method for Template Acquisition with Atrial Pacing

Figure 13:
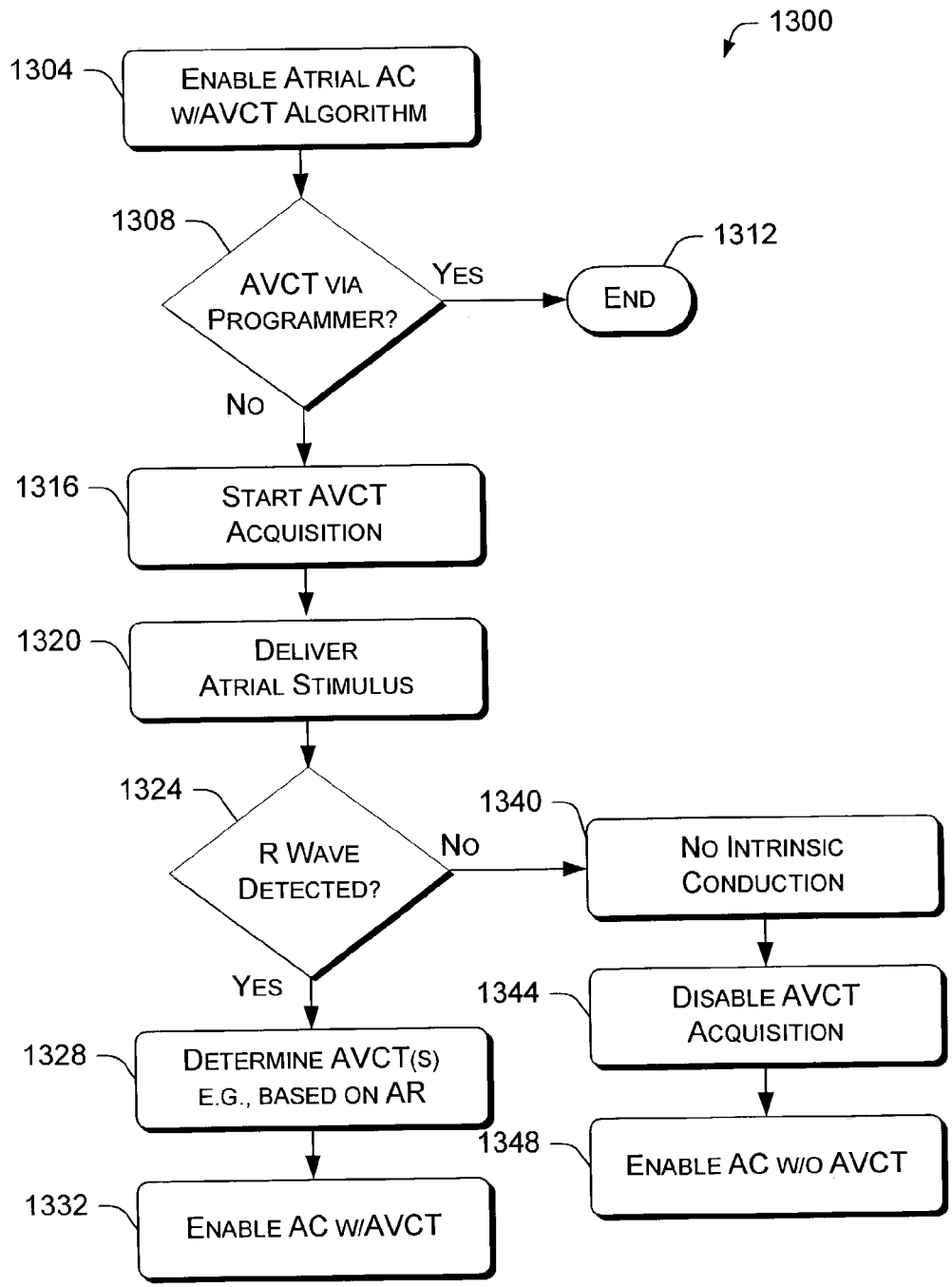
FIG. 13 is a block diagram of an exemplary method for determining AV conduction templates and/or other suitable information for use in an atrial autocapture scheme wherein the templates and/or other information are collected in response to one or more atrial stimuli.

Referring to FIG. 13, an exemplary method 1300 for template acquisition with atrial pacing is shown. Of course, such a method may also be modified to acquire information other than information in the form of a template. In an enable block 1304, the method 1300 enables atrial autocapture and an AV conduction template (AVCT) algorithm. Next, in a decision block 1308, the method 1300 determines whether AV conduction template acquisition is available via a programmer. If the decision block 1308 determines that one or more AVCTs are available via a programmer (e.g., only available via a programmer and not through in vivo acquisition), then the method 1300 terminates in an end block 1312. In this instance, a programmer may provide one or more AVCTs and the atrial autocapture scheme or other suitable scheme continues.

If the decision block 1308 determines that one or more AVCTs are acquirable, then the method 1300 continues in a start AVCT acquisition block 1316. A delivery block 1320 follows that delivers an atrial stimulus having a relative certainty of producing atrial capture. Following the delivery block 1320, the method 1300, in another decision block 1324, determines whether an R wave was detected on a ventricular sensing channel (or other suitable channel) wherein the R wave corresponds to the delivered atrial stimulus, for example, after a predetermined interval. If no corresponding R wave is detected, then, in a determination block 1340, the method 1300 determines that intrinsic conduction is lacking or insufficient. For example, a patient may have a high degree of AV block or other AV nodal inadequacy. If AV conduction is insufficient, then in a disable block 1344, the method 1300 disables AVCT acquisition. An enable block 1348 follows the disable block 1344 wherein atrial autocapture is enabled without use of AVCTs.

If the decision block 1324 detects a corresponding R wave, then a determination block 1328 determines or acquires one or more AVCTs. For example, the one or more AVCTs are optionally based on an A wave to R wave interval (ARI). Following determination or acquisition of the one or more AVCTs, the method 1300, in an enable block 1332, enables atrial autocapture with use of AVCTs.

Exemplary Method for Template Acquisition without Atrial Pacing

Figure 14:
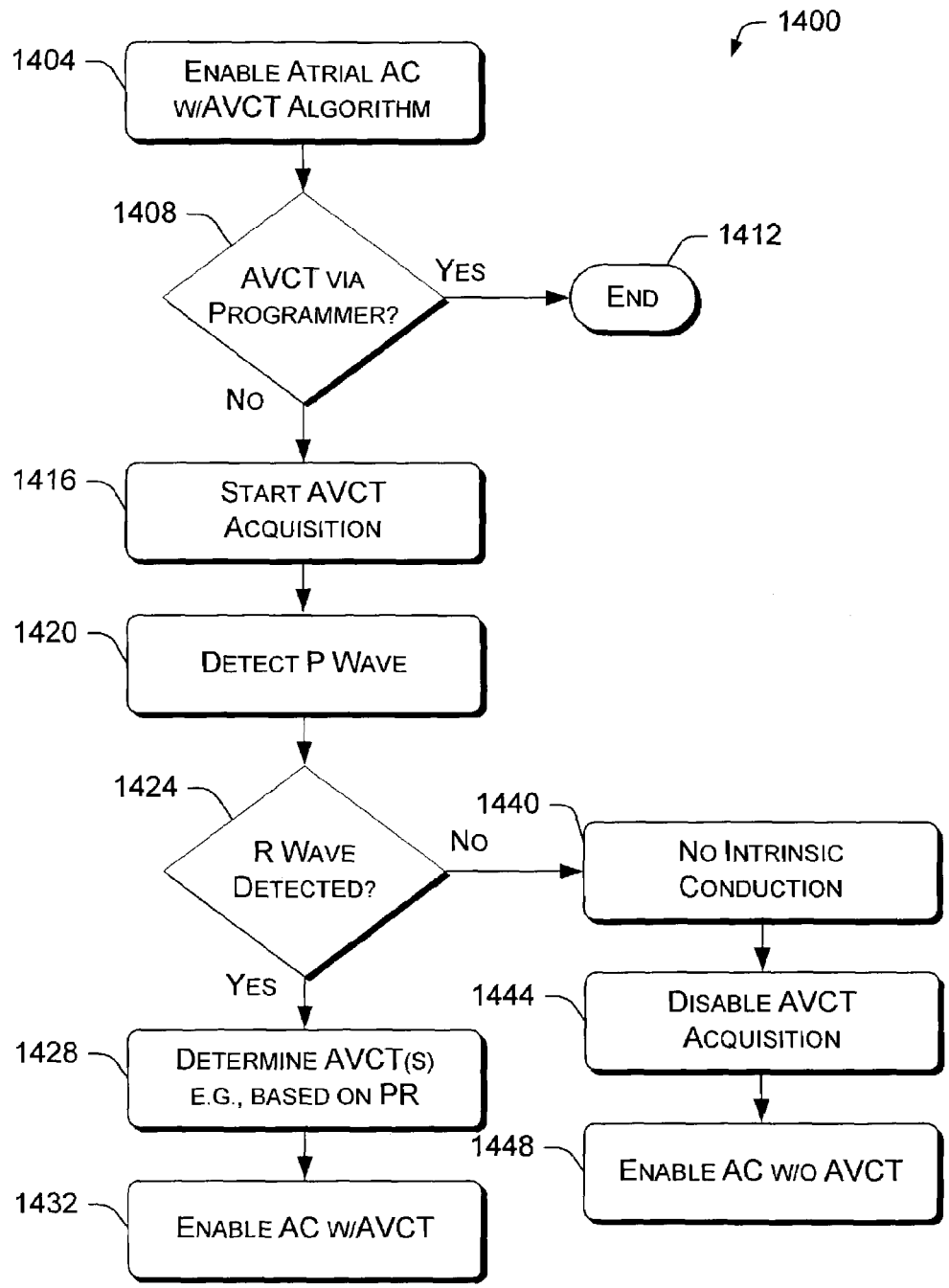
FIG. 14 is a block diagram of an exemplary method for determining AV conduction templates and/or other suitable information for use in an atrial autocapture scheme wherein the templates and/or other information are collected in response to native atrial activity.

Referring to FIG. 14, an exemplary method 1400 for template acquisition without atrial pacing is shown. Of course, such a method may also be modified to acquire information other than information in the form of a template. In an enable block 1404, the method 1400 enables atrial autocapture and an AV conduction template (AVCT) algorithm. Next, in a decision block 1408, the method 1400 determines whether AV conduction template acquisition is available via a programmer. If the decision block 1408 determines that one or more AVCTs are available via a programmer (e.g., only available via a programmer and not through in vivo acquisition), then the method 1400 terminates in an end block 1412. In this instance, a programmer may provide one or more AVCTs and the atrial autocapture scheme or other suitable scheme continues.

If the decision block 1408 determines that one or more AVCTs are acquirable, then the method 1400 continues in a start AVCT acquisition block 1416. A P wave detect block 1420 follows that detects a native P wave. Following the P wave detect block 1420, the method 1400, in another decision block 1424, determines whether an R wave was detected on a ventricular sensing channel (or other suitable channel) wherein the R wave corresponds to the detected P wave. If no corresponding R wave is detected, then, in a determination block 1440, the method 1400 determines that intrinsic conduction is lacking or insufficient. For example, a patient may have a high degree of AV block or other AV nodal inadequacy. If AV conduction is insufficient, then in a disable block 1444, the method 1400 disables AVCT acquisition. An enable block 1448 follows the disable block 1444 wherein atrial autocapture is enabled without use of AVCTs.

If the decision block 1424 detects a corresponding R wave, then a determination block 1428 determines or acquires one or more AVCTs. For example, the one or more AVCTs are optionally based on a P wave to R wave interval (PRI). Following determination or acquisition of the one or more AVCTs, the method 1400, in an enable block 1432, enables atrial autocapture with use of AVCTs.

Exemplary Method for Atrial Autocapture

Figure 15:
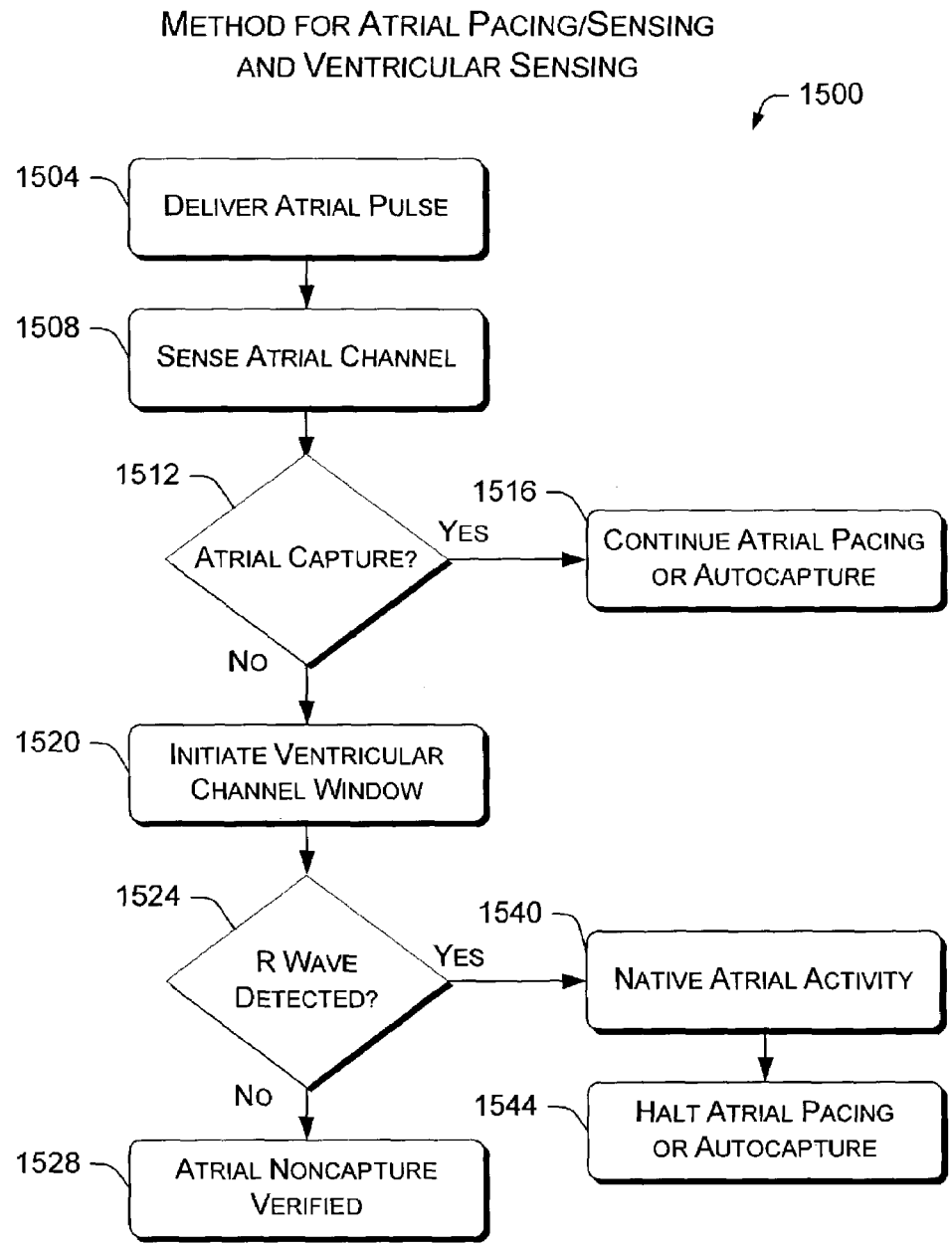
FIG. 15 is a block diagram of an exemplary method for determining whether atrial noncapture, atrial fusion, atrial pseudofusion, and/or atrial native activity occurred in response to an atrial stimulus wherein a back-up stimulus or termination of atrial pacing and/or atrial autocapture follow depending on the diagnosis.

Referring to FIG. 15, an exemplary method 1500 for atrial autocapture is shown. In a delivery block 1504, a pacing device delivers an atrial stimulus. Next, in a sense block 1508, an atrial sensing channel (or other suitable channel) senses atrial activity following the atrial stimulus. A decision block 1512 follows that determines whether atrial capture was sensed on the atrial sensing channel. If atrial capture was sensed, then the method 1500 continues atrial pacing and/or atrial autocapture. If the decision block 1512 determines that no atrial capture was sensed on the atrial sensing channel, then an initiation block 1520 follows, wherein a ventricular sensing channel window is initiated. The timing of the initiation and/or the duration of the window are optionally determined on the basis of information such as, but not limited to, atrial pacing rate, autonomic activity and/or tone, templates, acquired data, etc. Further, the method 1500 may deliver an atrial back-up pulse based on a determination of no atrial capture (e.g., at the end of the ventricular sensing window, etc.). Of course, the timing of such a pulse may also affect parameters associated with the ventricular sensing window. Alternatively, an atrial back-up pulse is implemented in a consequent cycle once atrial noncapture has been verified (e.g., see verification block 1528). Delivery of an atrial back-up pulse may also depend on whether there is a lack of native atrial activity (see e.g., decision block 1540 below).

Following initiation of the ventricular sensing channel window, another decision block 1524 determines whether an R wave was sensed in the window. If the decision block 1524 determines that an R wave was sensed, then, in a determination block 1540, the method 1500 determines that native atrial activity was present. Of course, if no R wave was sensed, then this may indicate a lack of native atrial activity. Again, an initial indication of noncapture followed by detection of an R wave can indicate that atrial fusion and/or atrial pseudofusion occurred (i.e., native atrial activity is present). A terminate atrial pacing and/or atrial autocapture block 1544 follows that terminates atrial pacing and/or atrial autocapture, which, in turn, may conserve power.

If the decision block 1524 determines that no R wave was sensed in the window, then, in a verification block 1528, the method 1500 verifies the result of the decision block 1512 (i.e., that no atrial capture occurred). In addition, a determination regarding native atrial activity may occur, for example, that there is no or inadequate native atrial activity. Further, in the instance that no R wave was sensed in the ventricular channel sensing window, an exemplary method may deliver a ventricular output at a set time or after a set delay (e.g., at the end of the AV interval) or it may start an AV interval coincident with delivery of a back-up atrial pulse.

Another Exemplary Method for Atrial Autocapture

Figure 16:
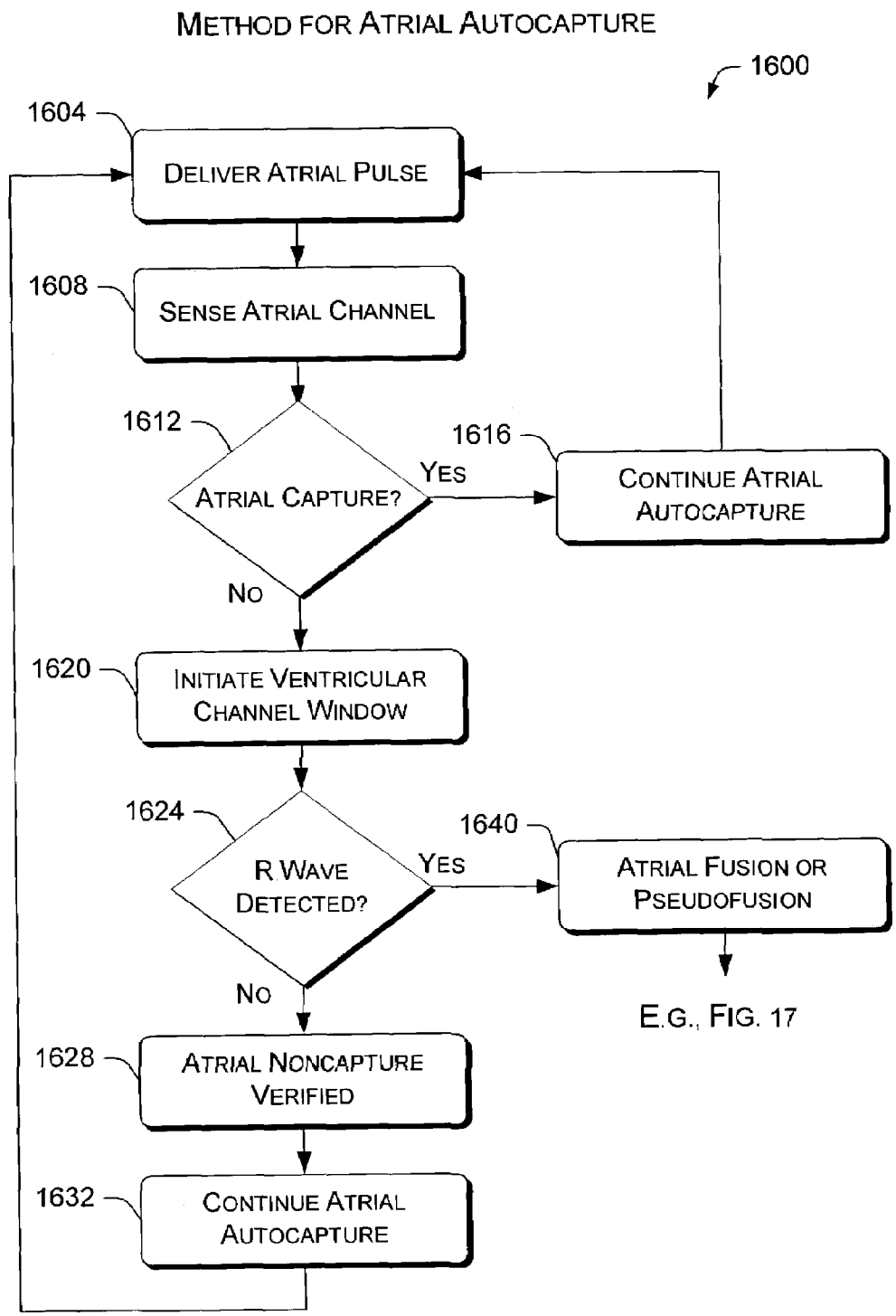
FIG. 16 is a block diagram of an exemplary method for determining whether atrial noncapture, atrial fusion, atrial pseudofusion, and/or atrial native activity occurred in response to an atrial stimulus wherein atrial quickening and/or atrial slowing and/or atrial autocapture follow depending on the diagnosis.

Referring to FIG. 16, an exemplary method 1600 for atrial autocapture is shown. In a delivery block 1604, a pacing device delivers an atrial stimulus. Next, in a sense block 1608, an atrial sensing channel (or other suitable channel) sensing atrial activity following the atrial stimulus. A decision block 1612 follows that determines whether atrial capture was sensed on the atrial sensing channel. If atrial capture was sensed, then the method 1600 continues atrial autocapture, for example, at the delivery block 1604 (as shown). If the decision block 1612 determines that no atrial capture was sensed on the atrial sensing channel, then an initiation block 1620 follows, wherein a ventricular sensing channel window is initiated. The timing of the initiation and/or the duration of the window are optionally determined on the basis of information such as, but not limited to, atrial pacing rate, autonomic activity and/or tone, templates, acquired data, etc.

Following initiation of the ventricular sensing channel window, another decision block 1624 determines whether an R wave was sensed in the window. If the decision block 1624 determines that an R wave was sensed, then, in a determination block 1640, the method 1600 determines that atrial fusion and/or atrial pseudofusion occurred. The method 1600 optionally continues corresponding to the exemplary method 1700 of FIG. 17.

If the decision block 1624 determines that no R wave was sensed in the window, then, in a verification block 1628, the method 1600 verifies the result of the decision block 1612 (i.e., that no atrial capture occurred). A continue atrial autocapture block 1632 follows wherein the atrial autocapture routine continues, for example, at the delivery block 1604. In general, the atrial stimulus power is increased if noncapture is verified. In addition, a back-up stimulus is optionally delivered on an atrial channel, a ventricular channel and/or other suitable channel.

Exemplary Method for Atrial Fusion and/or Atrial Pseudofusion

Figure 17:
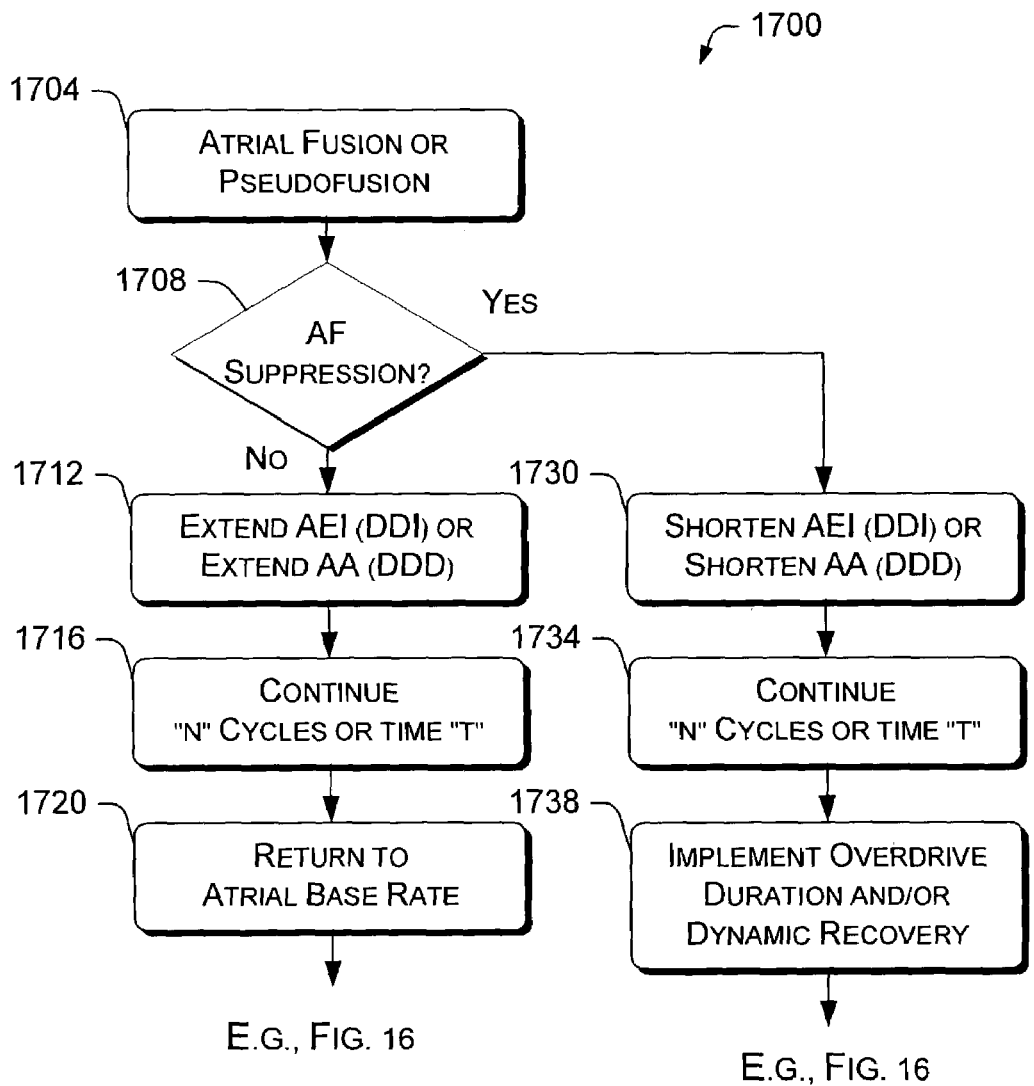
FIG. 17 is a block diagram of an exemplary method for atrial quickening and/or atrial slowing.

Referring to FIG. 17, an exemplary method 1700 for atrial fusion and/or atrial pseudofusion is shown. The method 1700 commences in an atrial fusion and/or atrial pseudofusion block 1704 (e.g., corresponding to the block 1640 of FIG. 16). A decision block 1708 follows that determines whether atrial fibrillation (AF) suppression is operable. If AF suppression is not operable, then in an extension block 1712, rate slowing occurs by, for example, extending AEI (e.g., for a DDI pacing scheme) or extending AA (e.g., for a DDD pacing scheme). The rate slowing continues in a continuation block 1716 wherein an extended AEI or AA is implemented for "n" cycles and/or a time "t". Following the continuation block 1716, the method 1700 returns atrial pacing at a base rate in a return block 1720. Following the return block 1720, the method 1700 continues, for example, with atrial pacing (see, e.g., the exemplary method 1600 of FIG. 16).

If the decision block 1708 determines that AF suppression is operable, then in a shorten block 1730, rate quickening occurs by, for example, shortening AEI (e.g., for a DDI pacing scheme) or shortening AA (e.g., for a DDD pacing scheme). The rate slowing continues in a continuation block 1734 wherein an extended AEI or AA is implemented for "n", cycles and/or a time "t". Following the continuation block 1734, the method 1700 implements overdrive duration and/or dynamic recovery in a post-quickening implementation block 1738. Overdrive is an increase in the atrial paced rate by a programmable rate in response to intrinsic sensed atrial activity. If there is stable pacing, this continues for a programmable number of cycles. Assuming that no detected P waves occurred during this period of overdrive pacing, according to this example, the pacing cycle progressively increases (rate slows) on each subsequent cycle until the system returns to the programmed base rate or the sensor-defined rate. It continues at this lower rate until additional native P waves are detected at which time, it again increases the base rate by the programmable overdrive rate (e.g., approximately 5 to 10 bpm above the functional rate). Following the implementation block 1738, the method 1700 continues, for example, with atrial pacing (see, e.g., the exemplary method 1600 of FIG. 16).

CONCLUSION

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

What is claimed is:

1. A method of determining whether atrial fusion and/or atrial pseudofusion occurred during atrial stimulation, the method comprising:
   monitoring for atrial activity in response to an atrial stimulus;
   determining that atrial capture did not occur if the atrial activity is not detected;
   initiating a ventricular sensing window for sensing ventricular activity responsive to the atrial stimulus;
   monitoring for ventricular activity responsive to the atrial stimulus in the ventricular sensing window; and
   deciding that atrial fusion and/or atrial pseudofusion occurred if ventricular activity responsive to the atrial stimulus was detected in the ventricular sensing window.

2. The method of claim 1 wherein the ventricular sensing window depends on atrial rate.

3. The method of claim 1 wherein the ventricular sensing window depends on autonomic activity and/or autonomic tone.

4. The method of claim 1 further comprising determining autonomic activity and/or autonomic tone.

5. The method of claim 1 further comprising controlling autonomic activity and/or autonomic tone.

6. A method of determining whether atrial fusion and/or atrial pseudofusion occurred during atrial autocapture comprising:
   monitoring for atrial activity responsive to an atrial stimulus;
   initially determining that atrial capture did not occur;
   monitoring for ventricular activity responsive to the atrial stimulus;
   determining whether ventricular activity responsive to the atrial stimulus was detected during the sensing;
   comparing the sensed ventricular activity responsive to the atrial stimulus to known information if ventricular activity was detected; and
   deciding whether atrial fusion and/or atrial pseudofusion occurred on the basis of the comparing.

7. The method of claim 6 wherein the known information depends on atrial rate.

8. The method of claim 6 wherein the known information depends on autonomic activity and/or autonomic tone.

9. The method of claim 6 further comprising determining autonomic activity and/or autonomic tone.

10. An implantable pacing device comprising:
    means for storing information related to ventricular activity responsive to an atrial stimulus;
    means for determining whether atrial capture occurs in response to an atrial stimulus;
    means for sensing ventricular activity responsive to an atrial stimulus; and
    means, responsive to a determination that atrial capture did not occur, for comparing sensed ventricular activity to the information to determine whether atrial fusion and/or atrial pseudofusion occurred.

11. The implantable pacing device of claim 10 wherein the means for storing comprises memory.

12. The implantable pacing device of claim 10 wherein the means for determining comprises one or more atrial sensing channels.

13. The implantable pacing device of claim 10 wherein the means for sensing ventricular activity comprises one or more ventricular sensing channels.

14. The implantable pacing device of claim 10 wherein the means for comparing comprises memory and a processor.

* * * * *